United States Patent
Roecker et al.

(10) Patent No.: US 12,427,159 B2
(45) Date of Patent: Sep. 30, 2025

(54) HYDROXYPYRROLIDINE-SUBSTITUTED ARYLSULFONAMIDE COMPOUNDS WITH SELECTIVE ACTIVITY IN VOLTAGE-GATED SODIUM CHANNELS

(71) Applicants: Merck Sharp & Dohme LLC, Rahway, NJ (US); Anthony J. Roecker, Harleysville, PA (US); Mark E. Layton, Harleysville, PA (US); Deping Wang, Furlong, PA (US); Xiu Wang, Shanghai (CN); Xuanjia Peng, Shanghai (CN)

(72) Inventors: Anthony J. Roecker, Harleysville, PA (US); Mark E. Layton, Harleysville, PA (US); Deping Wang, Furlong, PA (US); Xiu Wang, Shanghai (CN); Xuanjia Peng, Shanghai (CN)

(73) Assignee: Merck Sharp & Dohme LLC, Rahway, NJ (US)

( * ) Notice: Subject to any disclaimer, the term of this patent is extended or adjusted under 35 U.S.C. 154(b) by 937 days.

(21) Appl. No.: 17/615,769

(22) PCT Filed: Jun. 8, 2020

(86) PCT No.: PCT/US2020/036554
§ 371 (c)(1),
(2) Date: Dec. 1, 2021

(87) PCT Pub. No.: WO2020/251872
PCT Pub. Date: Dec. 17, 2020

(65) Prior Publication Data
US 2022/0305035 A1    Sep. 29, 2022

(30) Foreign Application Priority Data

Jun. 11, 2019    (WO) ................ PCT/CN2019/090712

(51) Int. Cl.
*A61K 31/635* (2006.01)
*C07D 417/12* (2006.01)
*C07D 417/14* (2006.01)

(52) U.S. Cl.
CPC .......... *A61K 31/635* (2013.01); *C07D 417/12* (2013.01); *C07D 417/14* (2013.01)

(58) Field of Classification Search
CPC ... C07D 417/12; C07D 417/14; A61K 31/635
See application file for complete search history.

(56) References Cited

U.S. PATENT DOCUMENTS

| | | |
|---|---|---|
| 6,664,400 B2 | 12/2003 | Taylor et al. |
| 9,546,164 B2 | 1/2017 | Andrez et al. |
| 9,586,968 B2 | 3/2017 | Layton et al. |
| 2018/0105504 A1 | 4/2018 | Sutherlin et al. |

FOREIGN PATENT DOCUMENTS

| | | |
|---|---|---|
| WO | 2009012242 A2 | 1/2009 |
| WO | 2010079443 A1 | 7/2010 |
| WO | 2012004706 A2 | 1/2012 |
| WO | 2012004714 A2 | 1/2012 |
| WO | 2012064984 A1 | 5/2012 |
| WO | 2013025883 A1 | 2/2013 |
| WO | 2013064983 A1 | 5/2013 |
| WO | 2013064984 A1 | 5/2013 |
| WO | 2013086229 A1 | 6/2013 |
| WO | 2013134518 A1 | 9/2013 |
| WO | 2017106226 A1 | 6/2017 |
| WO | 2018081384 A1 | 5/2018 |

OTHER PUBLICATIONS

Wu, Yong-Jin et al., Development of New Benzenesulfonamides As Potent and Selective Nav1.7 Inhibitors for the Treatment of Pain, Journal of Medicinal Chemistry, 2017, 2513-2525, 60.
Baker et al., Involvement of Na + Channels in Pain Pathways, Trends in Pharmacological Sciences, 2001, 27-31, 22, No. 1.
Benyamin et al., Opioid Complications and Side Effects, Pain Physician, 2008, 105-120, 11.
Berge, S.M., et al.,, "Pharmaceutical Salts", J. Pharm. Sci, 1977, pp. 1-19, vol. 66, No. 1.
Bingham, A.L., et al.,, "Over One Hundred Solvates of sulfathiazole", Chem. Commun., 2001, pp. 603-604.
Caira, M.R., et al.,. "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.

(Continued)

*Primary Examiner* — Rebecca L Anderson

(74) *Attorney, Agent, or Firm* — Sylvia A. Ayler; Catherine Fitch

(57) ABSTRACT

Disclosed are compounds of Formula A, or a salt thereof: Wherein "A¹", R¹, R², R³, R⁶, and R⁷ are as defined herein, which compounds have properties for blocking Nav 1.7 ion channels found in peripheral and sympathetic neurons. Also described are pharmaceutical formulations comprising the compounds of Formula A or their salts, and methods of treating cough, itch and neuropathic pain disorders using the same.

Formula A

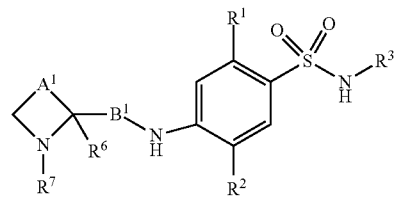

15 Claims, No Drawings

(56) References Cited

OTHER PUBLICATIONS

Carter et al., Advances in the Management of Neuropathic Pain, Physical Medicine and Rehabilitation Clinics of North America, 2001, 447-459, 12(2).
Chong et al., Comparison of Lidocaine and Bronchodilator Inhalation Treatments for Cough Suppression in Patients with Chronic Obstructive Pulmonary Disease, Emerg Med J., 2005, 429-432, 6.
Clare et al., Voltage Gated Sodium Channels as Therapeutic Targets, Therapeutic Focus, 2000, 506-520, 5.
Cox et al., Toxicity of Local Anaesthetics, Best Practices & Research Clinicial Anaesthesiology, 2003, 111-136, 17, No. 1.
Devigili et al., Paroxysmal Itch Caused by Gain of Function Nav1/7 Mutation, Pain, 2014, 1702-1707, 155.
Flaxman et al., Years Lived with Disability (YLDs) for 1160 Sequelae of 289 Diseases and Injuries 1990-2010: A Systematic Analysis for the Global Burden of Disease Study 2010, Lancet, 2012, 2163-2196, 380.
Goldin et al., Nomenclature of Voltage-Gated Sodium Channels, Neuron, 2000, 365-368, 28.
Goldin, Diveristy of Mammalian Voltage-Gated Sodium Channels, Ann NY Acad Sci., 1999, 38-50, 30, 868.
Gould, Salt selection for basic drugs, International J. of Pharmaceutics, 1986, 201-217, 33.
Hansson et al., Effects of Inhaled Lignocaine and Adrenaline on Capsaicin Induced Cough in Humans, Thorax, 1994, 1166-1168, 49.
Ikoma et al., The Neurobiology of Itch, Nature Reviews, 2006, 535-547, 7.
Irwin et al., The Diagnosis and Treatment of Cough, New England J. of Medicine, 2000, 1715-1721, 343 (23).
Klinger et al., Sea-Anemone Toxin ATX-II Elicits A-Fiber-Dependent Pain and Enhances Resurgent and Persistent Sodium Currents in large Sensory Neurons, Molecular Pain, 2012, 1-17, 8:69.
Lee et al., A Monoclonal Antibody that Targets a Nav1.7 Channel Voltage Sensor for Pain and Itch Relief, Cell, 2014, 1-12, 157.
Mcmahon et al., Itching for an Explanation, Trends Neuroscience, 1992, 497-501, 15.

Morice et al., Opiate Therapy in Chronic Cough, Am J. Respir Crit Care Med., 2007, 312-315, 175.
Muroi et al., Selective Inhibition of Vagal Afferent Nerve Pathways Regulating Cough Using Nav 1.7 shRNA Silencing in Guinea Pig Nodose Ganglia, Am. J. Physiol Regul Interg Comp Physiol, 2013, R1017-R1023, 301.
Muroi et al., Targeting Voltage Gated Sodium Channels Nav1.7 Nav 1.8, and Nav 1.9 for Treatment of Pathological Cough, Lung, 2014, 15-20, 192.
Nasra et al., Modulation of Sensory Nerve Function and the Cough Reflex: Understanding Disease Pathogenesis, Pharmacology & Therapeutics, 2009, 354-375, 124.
Nassar et al., Nociceptor Specific Gene Deletion REveals a Major Role for Nav1.7 (PN1) In Acute and Inflammatory Pain, Proc. Nat. Acad. Sci, 2004, 12706-12711, 101 (34).
Rook et al., Biology of Cardiac Sodium Channel Nav1.5 Expression, Cardiovascular Research, 2012, 12-23, 93.
Schmelz et al., Specific C-Receptors for Itch in Human Skin, J. of Neuroscience, 1997, 8003-8008, 17(20).
Smith et al., Effect of Codeine on Objective Measurement of Cough in Chronic Obstructive Pulmonary Disease, J. of Allergy and Clinical, 2006, 831-835, 117.
Stahl et al., Aminoquinazoline Compounds as A2A Antagonist, Handbook of Pharmaceutical Salts Properties, Selection, and Use, 2002, 330-331.
Takahama et al., Central and Peripheral Mechanisms of Narcotic Antitussives: Codeine Sensitive and Resistant Coughs, Cough, 2007, 1-8, 3:8.
Van Loey et al., Itching Following Burns: Epidemiology and Predictors, British J. Dermatology, 2008, 95-100, 158.
Van Tonder, E.C., et al.,, "Preparation and Physicochemical Characterization of 5 Niclosamide Solvates and 1 Hemisolvate", AAPS Pharm Sci Tech, 2004, pp. 1-10, vol. 5, No. 1, Article 12, US.
Waxman et al., Na, 1.7- Related Small Fiber Neuropathy, Neurology, 2012, 1635-1643, 78 (21).
Wood et al., Voltage-Gated Sodium Channels and Pain Pathways, J. Neurobiol., 2004, 55-71, 61.
Yu et al., Overview of the Voltage-Gated Sodium Channel Family, Genome Biology, 2003, 207, 4.

HYDROXYPYRROLIDINE-SUBSTITUTED ARYLSULFONAMIDE COMPOUNDS WITH SELECTIVE ACTIVITY IN VOLTAGE-GATED SODIUM CHANNELS

CROSS REFERENCE TO RELATED APPLICATIONS

This application is a U.S. National Phase application under 35 U.S.C. § 371 of PCT Application No. PCT/US2020/036554 filed Jun. 8, 2020 which claims priority to Application No. PCT/CN2019/090712 filed Jun. 11, 2019.

BACKGROUND

Voltage-gated sodium channels play a central role in initiating and propagating action potentials in electrically excitable cells such as neurons and muscle, see for example Yu and Catterall, Genome Biology 4:207 (2003) and references therein. Voltage-gated sodium channels are multimeric complexes characterized by an Alpha-subunit which encompasses an ion-conducting aqueous pore, and is the site of the essential features of the channel, and at least one Beta-subunit that modifies the kinetics and voltage-dependence of the channel gating. These structures are ubiquitous in the central and peripheral nervous system where they play a central role in the initiation and propagation of action potentials, and also in skeletal and cardiac muscle where the action potential triggers cellular contraction. (see Goldin, Ann NY Acad Sci. 30; 868:38-50 (1999)).

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.), with the number designator X (1 to 9) being assigned for the alpha subunit present in the structure (see Aoldin et al., Neuron, 28:365-368 (2000)). $Na_v1.7$ voltage-gated sodium ion channels (herein designated "Nav 1.7 channels" in some instances for convenience) are expressed primarily in sensory and sympathetic neurons, are believed to play a role in various maladies, for example, nociception, cough, and itch, and in particular have a central role in inflammatory pain perception, (see Wood et al. J. Neurobiol. 61: pp 55-71 (2004), Nassar et al., *Proc. Nat. Acad. Sci.* 101(34): pp 12706-12711 (2004), Klinger et. al., Molecular Pain, 8:69 (2012), Devigili et. al., Pain (in press), http://dx.doi.org/10.1016/j.pain.2014.05.006 (2014), Lee et. al., Cell, 157:1-12 (2014), Muroi et. al., Lung, 192:15-20 (2014), Muroi et. al., Am J Physiol Regul Integr Comp Physiol 304:R1017-R1023 (2013)). Accordingly, it is believed that identification and administration of agents which interact to block $Na_v$ 1.7 voltage-gated sodium ion channels represents a rational approach for providing treatment or therapy for disorders involving $Na_v1.7$ receptors, for example, nociceptive, cough, or itch disorders, as well as those stemming specifically from dysfunction of $Na_v1.7$ voltage-gated sodium ion channels (see Clare et al., Drug Discovery Today, 5: pp 506-520 (2000)).

It has been shown in human patients as well as in animal models of neuropathic pain that damage to primary afferent sensory neurons can lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31.

Cough is one of the most prevalent symptoms for which patients seek the attention of their primary care physicians; chronic cough for example is estimated to affect approximately 40% of the population. The fundamental mechanisms of the cough reflex are complex and involve an array of events initiated by the activation of airway sensory nerves that physically results in a forced expiration of the airways. This protective reflex is necessary to remove foreign material and secretions from the airways, however, chronic, non-protective cough results in a dramatic negative impact on quality of life (see Nasra et. al., Pharmacology & Therapeutics, 124(3):354-375 (2009)).

Cough symptoms can arise from the common cold, allergic and vasomotor rhinitis, acute and chronic bacterial sinusitis, exacerbation of chronic obstructive pulmonary disease, *Bordetella pertussis* infection, asthma, postnasal-drip syndromes, gastroesophageal reflux disease, eosinophilic and chronic bronchitis, and angiotensin-converting-enzyme inhibitors, cough is categorically described as acute, subacute, or chronic, respectively lasting less than three weeks, three to eight weeks, and more than eight weeks in duration (see Irwin et. al., The New England Journal of Medicine, 343(23):1715-1721 (2000)).

Current standard of care for the treatment of cough consists of centrally and peripherally acting suppressants such as opioids and local anaesthetics respectively, both of which are dose-limited by side-effects (see Cox et. al., Best Practice & Research Clinical Anaesthesiology, 117(1):111-136 (2003) and Benyamin et. al., Pain Physician, 11:S105-S120 (2008)). Opioids primarily act on μ-opioid receptors of the central nervous system, and in some reports, also on peripheral afferents of the cough reflex arc—they exhibit varied degrees of efficacy and are limited by side-effects such as sedation, physical dependence, and gastrointestinal problems; morphine has shown to be an effective treatment for chronic cough (see Morice et. al., Am J Respir Crit Care Med 175:312-315 (2007) and Takahama et. al., Cough 3:8 (2007)), but is generally restricted to patients with terminal illness such as lung cancer. Codeine, found in some cough syrups, and also administered systemically, was found no more effective than placebo (see Smith et. al., Journal of Allergy and Clinical Immunology, 117:831-835 (2006). Local anesthetics act peripherally by reducing the generation of action potentials in sensory nerves of the airway as result of non-selectively blocking all voltage gated sodium channel subtypes and have demonstrated varied degrees of efficacy in treating cough—they are often found in over-the-counter lozenges and have been shown to relieve cough when administered via nebulisation (see Nasra et. al., Pharmacology & Therapeutics, 124(3):354-375 (2009) and Hansson et. al., Thorax, 49(11):1166-1168 (1994)), however, in a study with chronic obstructive pulmonary disease patients, lidocaine was not effective (see Chong et. al., Emerg Med J, 22(6):429-32 (2005)).

In pre-clinical animals, NaV1.7, NaV1.8, and NaV1.9 were determined to be the primary voltage-gated sodium channels expressed in the afferent nerves of the respiratory tract (see Muroi et. al., Lung, 192:15-20 (2014)) and in animal models of cough, suppression of NaV1.7 function resulted in a marked decrease in number of coughs (see Muroi et. al., Am J Physiol Regul integr Comp Physiol, 304:R1017-R0123 (2013)), thus, combined with previous evidence that local anesthetics can be effective antitussive agents, the targeted blockade of NaV1.7 channels represents a rational approach for the treatment of cough with a preferential side-effect profile as compared to local anesthetics, which undesirably inhibit all voltage gated sodium channels, such as NaV1.5 channels which are found in heart muscle (see Rook et. al., Cardiovascular Research 93:12-23 (2012)).

Pruritus, also commonly known as itch, affects approximately 4% of the global population (see Flaxman et. al., Lancet, 380:2163-2196 (2012)) is "an unpleasant sensation that elicits the desire or reflex to scratch" and is regarded as closely related to pain. Theories on the origin of itch implicate the subtle, low-frequency activation of nociceptors (pain-sensing neurons), however, it has been described that some afferents preferentially respond to histamine, which induces itch (see Schmelz et. al., J Neuroscience, 17(20): 8003-8008 (1997)). At the same time, it has been found that histamine-responding neurons also respond to capsaicin which produces pain (see McMahon et. al., Trends. Neurosci., 15:497-501 (1992)). Members of the transient receptor potential (TRP) family, and nerve growth factor (NGF) are both known to play a role in itch and pain, and clinically, both maladies are treated with therapeutic agents such as gabapentin and antidepressants—as such, it continues to be accepted that the underlying mechanisms of pain and itch are highly interwoven and complex, and distinguishing pan-selective or itch-selective pathways remains ambiguous (see Ikoma et. al., Nature Reviews Neuroscience, 7:535-547 (2006)).

Itch, both chronic and acute, can arise from many different insults and diseases and may be classified as dermal or pruriceptive, neurogenic, neuropathic, or psychogenic: itch can arise from both systemic disorders, skin disorders, as well as physical or chemical insult to the dermis. Pathologically, conditions such as dry skin, eczema, psoriasis, varicella zoster, urticaria, scabies, renal failure, cirrhosis, lymphoma, iron deficiency, diabetes, menopause, polycythemia, uremia, and hyperthyroidism can cause itch, as can diseases of the nervous system such as tumors, multiple sclerosis, peripheral neuropathy, nerve compression, and delusions related to obsessive-compulsive disorders. In skin, pruritogens are released from keratinocytes, lymphocytes, mast cells, and eosinophils during inflammation—these molecules act directly on free nerve endings to induce itch; medicines such as opioids and chloroquine can also trigger itch (see Ikoma et. al., Nature Reviews Neuroscience, 7:535-547 (2006)). Itching following burn is also an extremely serious clinical problem as it hampers the healing process, results in permanent scaring, and negatively impacts quality of life (see Loey et. al., British Journal of Dermatology, 158:95-100 (2008)).

Gain of function mutations of NaV1.7 have been found in approximately 28% of patients with idiopathic small fiber neuropathy (I-SFN); these mutations were found to render dorsal root ganglia neurons hyperexcitable—reducing the threshold of activation, and increasing the frequency of evoked firing (see Waxman et. al., Neurology, 78(21):1635-1643 (2012)). Severe, uncontrollable itch has also been genetically linked to a gain-of-function mutation (I739V) in the sodium channel NaV1.7 in man (see Devigili et. al., Pain (in press), http://dx.doi.org/10.1016/j.pain.2014.05.006 (2014)). Additionally, the sea-anemone toxin ATX-II has been found to elicit pain and itch in human volunteers after intradermal injection on the forearm; electrophysiology studies revealed that ATX-II enhanced NaV1.7 and NaV1.6 resurgent currents (see Klinger et. al., Molecular Pain, 8:69 (2012)). It has been demonstrated in animal models that selective blockade of NaV1.7 channels can effectively suppress both inflammatory and neuropathic pain, as well as acute and chronic itch, thus blockade of NaV1.7 channels represents a rational approach to treatment of pain and itch disorders (see Lee et. al., Cell, 157:1-12 (2014)).

Because voltage gated sodium ion channels are ubiquitous in the central and peripheral nervous system, as well as in both cardiac and skeletal muscle, and conservation of structures in the various Alpha-subunits characterizing voltage-gated sodium ion channels implicates the potential for producing serious side effects when utilizing therapeutic agents having a mechanism of action that target blocking voltage-gated sodium ion channels, for example, therapeutic agents suitable for use in addressing nociception, cough, or itch disorders, requires therapeutic agents having specificity in their action, for example, in discriminating between action upon $Na_v1.5$ sodium ion channels, thought to be important in regulation of cardiac function and action upon $Na_v1.7$ sodium ion channels, thought to be central in inflammatory nociception, cough, or itch and disorders arising from dysfunctional $Na_v$ 1.7 sodium ion channels.

Published international application no. WO09/012242 (the '242 publication) describes compounds having the structure of Formula PA:

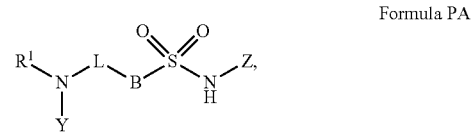

Formula PA wherein $R^1$ is a proton, alkyl or heteroalkyl, aryl, or heteroaryl group, Y is an aryl group or a 5 or 6 member-ring heteroaryl group, L is either not present or is a cyclic structure containing nitrogen or substituted with nitrogen, B is a cycloalkyl, heterocycloalkyl, aryl or heteroaryl moiety, and Z is a five or six-member ring heteroaryl moiety, and optionally R*, N, and Y form a cyclic structure which may be a heteroaryl moiety, for example, the compound of Formula PB:

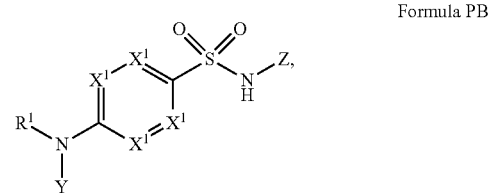

Formula PB wherein $R^1$, Y, and Z are as defined for the compound of Formula PA, and wherein each $X^1$ is independently N or unsaturated carbon optionally substituted with hydrogen, halogen, CN, OH, alkyl or substituted alkyl. These compounds are said to have activity as Nav 1.7 channel and Nav 1.3 channel blockers but are not shown to have selectivity as specific Nav 1.7 channel blockers.

Published international application WO 2013/025883 (the '883 publication) and WO2013/086229 (the '229 publication) describes compounds having the structure of Formula PC:

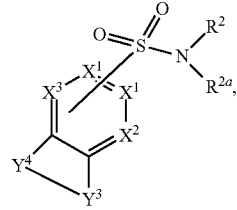

Formula PC

Wherein the aminosulfonyl moiety is bonded to one of $X^1$ and the other of $X^1$ is [=N-] or [=CR$^3$—] (R$^3$ is a wide number of substituents including alkyl and halogen), one of $R^{2a}$ or $R^{2b}$ is an aryl or heteroaryl moiety and the other is —H or alkyl, and $Y^3$-$Y^4$ form a 5 or 6 member unsaturated ring which may contain one or more nitrogen atoms and may be substituted on one or more ring atoms.

Compounds having Na$_v$1.7 activity described in published international applications WO 2010/079443 (the '443 publication) and related WO2012/004706, WO2012/004714, WO2012/064984, WO2013/064983, and WO2013/064984 have the structure of Formula PD:

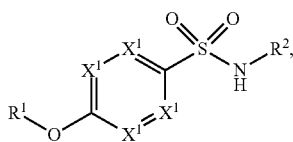

Formula PD wherein $X^1$ is [=N-] or [=CR$^3$—], —R$^3$ is a wide number of substituents including halogen, R$^1$ is a cycloalkyl, aryl or heteroaryl moiety and R$^2$ is a heteroaryl moiety.

Examples of these compounds include compounds of Formula PE:

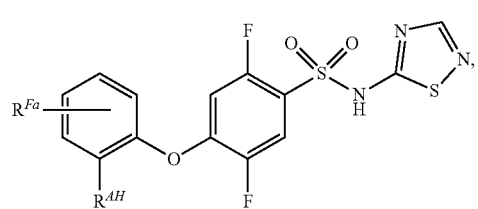

Formula PE where $R^{AH}$ is an aryl or heteroaryl moiety and $R^{Fa}$ is one or more of a wide variety of substituents, for example the hetero-substituted aryl compounds of Formula PF:

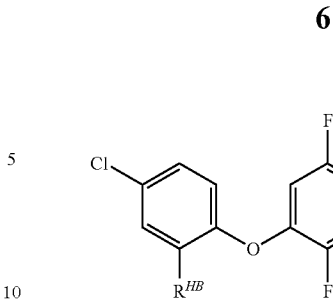

Formula PF wherein $R^{HB}$ is a heterobicyclo moiety, and Formula PG:

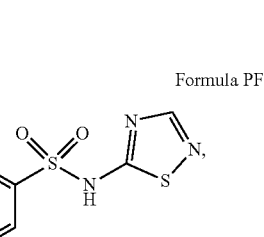

Formula PG

An additional example of these compounds are the heterocycloalkyl-substituted compounds of Formula PH:

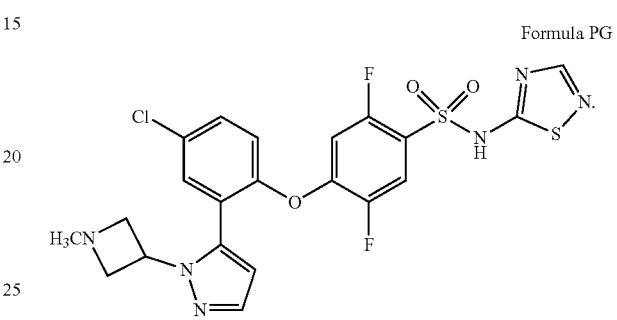

Formula PH

Wherein at least one of $X^{1F}$ and $X^{2F}$ are a heteroatom and the other is either a substituted carbon or CH, $R^{AH}$ is an aryl or heteroaryl moiety and $R^{Fa}$ is one or more of a wide variety of substituents. These foregoing compounds are said to have affinity for Nav 1.7 sodium channels and modest or low affinity for Na$_v$1.5 sodium channels, but do not offer much structural diversity.

Recently, compounds described in published international applications WO 2013/025883 WO2013/086229, and WO2013/134518, having the structure of Formula PJ$^1$ or PJ$^2$:

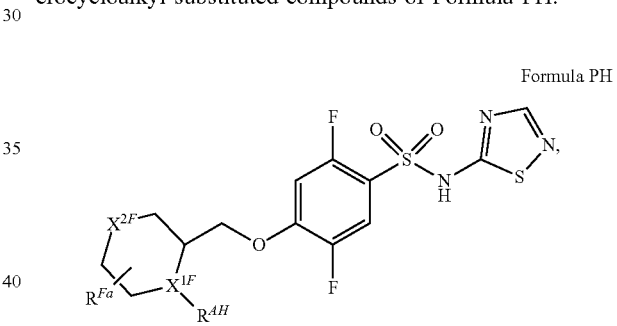

Formula PJ$^1$

Wherein one of $R^{2a}$ or $R^{2b}$ is an aryl or heteroaryl moiety and the other is —H or alkyl, $X^3$ to $X^5$ are =N— or =CR$^5$— (where R$^5$ is a wide range of compatible substituents), $X^{1a-1d}$ are [=N—], —NR$^4$— (where R$^4$ is H, alkyl, or a wide variety of other substituents compatible with N), or [=CR$^3$—] (R$^3$ is a wide number of substituents, including, H, alkyl, aryl and heteroaryl) and wherein $X^{1c}$ may be absent, in which case $X^{1b}$ is CH; or

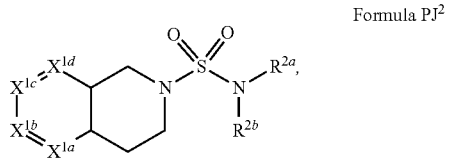

Formula PJ$^2$

Wherein one of R$^{2a}$ or R$^{2b}$ is an aryl or heteroaryl moiety and the other is —H or alkyl, and $X^{1a-1d}$ are [=CR$^3$—] (R$^3$ is a wide number of substituents, including, H, or alkyl, aryl and heteroaryl, of which the latter three may have a wide variety of substituents). These compounds claim activity for Nav1.7 sodium ion channels and selectivity over Nav1.5 channels.

There remains a need for additional compounds having both high potency for blocking Na$_v$ 1.7 sodium ion channels and selective activity for Na$_v$ 1.7 sodium ion channels, while having also acceptable bioavailability properties, and which provide a variety of cores to facilitate rational development of therapeutic agents for use as selective Na$_v$ 1.7 sodium ion channel.

SUMMARY OF THE INVENTION

In one aspect, the invention provides compounds having selective activity as Na$_v$ 1.7 sodium ion channel blockers which have the structure of Formula A, or a salt thereof:

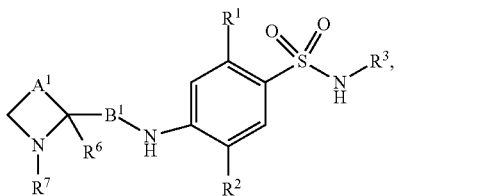

Formula A wherein:
B$^1$ is —(CR$^4$R$^5$)$_m$—,
wherein:
"m" is 1 or 2;
R$^4$ and R$^5$ are independently for each occurrence: (i) —H; (ii) a cyclic-, branched-, or linear-alkenyl moiety of up to 6 carbon atoms; (iii) a cyclic-, branched- or linear-alkyl moiety of up to 6 carbon atoms, which alkyl moiety is optionally substituted by one or more substituents which are independently:
 (a) an aryl moiety of up to 10 carbon atoms which aromatic moiety is optionally substituted up to 3 substituents which are independently for each occurrence: (1) cyclic-, branched-, or linear-alkyl moiety of up to 4 carbon atoms which is optionally substituted with —N(R$^{1a}$)$_2$, wherein "R$^{1a}$" is independently for each occurrence: H; or linear-, branched, or cyclic-alkyl of up to 4 carbon atoms; (2) branched-, or linear-alkoxy moiety of up to 4 carbon atoms; (3) halogen; (4) —CN; or (v) —N(R$^{2a}$)$_2$, wherein "R$^{2a}$" is independently for each occurrence: H; or linear-, branched, or cyclic-alkyl of up to 4 carbon atoms;
 (b) a heteroaryl moiety, as defined herein, comprising up to 5 carbon atoms and at least one ring atom which is N, O, or S, which heteroaryl moiety is optionally substituted with up to 3 substituents which are, independently: (1) cyclic-, branched-, or linear-alkyl moiety of up to 4 carbon atoms which is optionally substituted with —N(R$^{3a}$)$_2$, wherein "R$^{3a}$" is independently for each occurrence: H; or linear-, branched, or cyclic-alkyl of up to 4 carbon atoms; (2) branched-, or linear-alkoxy moiety of up to 4 carbon atoms; (3) halogen; (4) —CN; or (v) —N(R$^{4a}$)$_2$, wherein "R$^{4a}$" is independently for each occurrence: H; or linear-, branched, or cyclic-alkyl of up to 4 carbon atoms
 (c) halogen;
 (d) —CN; or
 (e) —N(R$^{5a}$)$_2$, wherein "R$^{5a}$" is independently for each occurrence: (1) H; (2) linear-, branched, or cyclic-alkyl of up to 4 carbon atoms;
A$^1$ is —(CR$^{10}$R$^{11}$)$_n$—, wherein:
"n" is 1, 2, or 3;
in at least one occurrence one of R$^{10}$ or R$^{11}$ is selected to be —OH; and
the remaining occurrences of R$^{10}$ and R$^{11}$ are independently for each occurrence:
 (a) hydrogen;
 (b) halogen, preferably —Cl or —F;
 (c) —OH;
 (d) —N(R$^{1e}$)$_2$, wherein "R$^{1e}$" is, independently for each occurrence, (i) —H; or (ii) lower alkyl;
 (e) a branched-, cyclic- or linear-alkyl moiety of up to 6 carbon atoms which is optionally substituted with one or more substituents which are, independently for each occurrence:
  (i) halogen, and when selected to be halogen is preferably —F or —Cl;
  (ii) —N(R$^{2e}$)$_2$, wherein "R$^{2e}$" is, independently for each occurrence: (1) —H; or (2) lower alkyl;
  (iii) —OH;
  (iv) an aryl moiety which is optionally substituted with one or more, independently, cyclic-, branched-, or linear-alkoxy moiety of up to 4 carbon atoms; or
  (v) a heteroaryl moiety comprising up to 5 carbon atoms and at least one heteroatom, and when selected to be a heteroaryl is preferable a 5-member heterocycle comprising at least one heteroatom which is N, S, or O, wherein said heteroaryl moiety is optionally substituted with one or more cyclic-, branched-, or linear-alkoxy moiety comprising up to 6 carbon atoms;
 (f) an aryl moiety which is optionally substituted with one or more substituents which are independently:
  i. a cyclic-, branched-, or linear-alkyloxy moiety of up to 4 carbon atoms; or
  ii. —OH; or
 (g) a heteroaryl moiety, as defined herein, comprising up to 5 carbon atoms and at least one heteroatom, and when selected to be a heteroaryl is preferable a 5-member heterocycle comprising at least one heteroatom which is N, S, or O, wherein said heteroaryl moiety is optionally substituted with one or more substituents which are independently: (i) —CN; (ii) —OH; (iii) halogen, preferably —F or —Br; (iv)

cyclic-, branched-, or linear-alkyl of up to 6 carbon atoms, which alkyl moiety is optionally substituted with: —OH; —CN; halogen; or —N($R^{13e}$)$_2$, wherein "$R^{13e}$" is, independently for each occurrence: —H or lower alkyl; or (iv) cyclic-, branched-, or linear-alkoxy of up to 6 carbon atoms, with the proviso that if "$R^{10}$" and "$R^{11}$" are selected to provide more than one occurrence of —OH, then the selection is made to preclude both germinal —OH and —OH depending from two adjacent carbon atoms;

$R^6$ is:
- (b) —H;
- (c) lower alkoxy;
- (d) a branched-, cyclic- or linear-alkyl of up to 6 carbon atoms which is optionally substituted with one or more substituents which are, independently for each occurrence:
  - i. halogen, and when selected to be halogen is preferably —F or —Cl;
  - ii. N($R^{2b}$)$_2$, wherein is, independently for each occurrence, —H or lower alkyl;
  - iii. lower alkyl;
  - iv. lower alkoxy;
  - v. an aryl moiety, as defined herein, comprising up to 6 ring carbon atoms, wherein the aryl ring of said moiety is optionally substituted with up to 3 substituents which are independently for each occurrence: (1) —CN; (2) —OH; (3) halogen, preferably —F or —Br; (4) cyclic-, branched-, or linear-alkyl of up to 4 carbon atoms, which alkyl moiety is optionally substituted with: —OH; —CN; halogen; or N($R^{3b}$)$_2$, wherein "$R^{3b}$" is, independently for each occurrence, —H or lower alkyl; (5) —N($R^{4b}$)$_2$, wherein "$R^{4b}$" is, independently for each occurrence, —H or lower alkyl; (6) cyclic-, branched-, or linear-alkoxy of up to 4 carbon atoms; (7) alkyl-thiol-moiety of up to 4 carbon atoms, and when selected to be a thiol moiety is preferably H$_3$C—S—; (8) alkyl-sulfonyl moiety of up to 4 carbon atoms, and when selected to be a sulfonyl moiety is preferably H$_3$C—S(O)$_2$—; or (9) a heterocycle moiety, as defined herein, comprising up to 5 carbon atoms and one or more heteroatoms which are N, O, or S;
  - vi. a heteroaryl moiety, as defined herein, comprising up to 4 carbon atoms and at least one heteroatom, and when selected to be a heteroaryl is preferably a 5-member heterocycle comprising at least one heteroatom which is N, S, or O, wherein said heteroaryl moiety is optionally substituted with one or more substituents which are independently: (a) —CN; (b) —OH; (c) halogen, preferably —F or —Br; (d) cyclic-, branched-, or linear-alkyl of up to 4 carbon atoms, which alkyl moiety is optionally substituted with: —OH; —CN; halogen; or N($R^{5b}$)$_2$, wherein "$R^{5b}$" is, independently for each occurrence, —H or lower alkyl; or (e) cyclic-, branched-, or linear-alkoxy of up to 4 carbon atoms;
- (e) an aryl moiety, as defined herein, comprising up to 6 ring carbon atoms, wherein the aryl ring of said moiety is optionally substituted with up to 3 substituents which are independently for each occurrence: (1) —CN; (2) —OH; (3) halogen, preferably —F or —Br; (4) cyclic-, branched-, or linear-alkyl of up to 4 carbon atoms, which alkyl moiety is optionally substituted with: —OH; —CN; halogen; or N($R^{1c}$), wherein "$R^{1c}$" is, independently for each occurrence, —H or lower alkyl; (5) —N($R^{2c}$)$_2$, wherein "$R^{2c}$" is, independently for each occurrence, —H or lower alkyl; (6) cyclic-, branched-, or linear-alkoxy of up to 4 carbon atoms; (7) alkyl-thiol-moiety of up to 4 carbon atoms, and when selected to be a thiol moiety is preferably H$_3$C—S—; (8) alkyl-sulfonyl moiety of up to 4 carbon atoms, and when selected to be a sulfonyl moiety is preferably H$_3$C—S(O)$_2$—; or (9) a heterocycle moiety, as defined herein, comprising up to 5 carbon atoms and one or more heteroatoms which are N, O, or S;
- (f) a heteroaryl moiety, as defined herein, comprising up to 4 carbon atoms and at least one heteroatom, preferably said heteroaryl moiety is a 5-member heterocycle comprising at least one heteroatom which is N, S, or O, wherein said heteroaryl moiety is optionally substituted with one or more substituents which are independently: (a) —CN; (b) —OH; (c) halogen, preferably —F or —Br; (d) cyclic-, branched-, or linear-alkyl of up to 4 carbon atoms, which alkyl moiety is optionally substituted with: —OH; —CN; halogen; or N($R^{3c}$)$_2$, wherein "$R^{3c}$" is, independently for each occurrence, —H or lower alkyl; or (e) cyclic-, branched-, or linear-alkoxy of up to 4 carbon atoms; or
- (g) a heterocycle moiety, as defined herein, comprising up to 5 carbon atoms and one or more heteroatoms which are N, O, or S.

$R^7$ is:
- (a) —H;
- (b) an cyclic-, branched-, or linear-alkyl moiety of up to 7 carbon atoms which is optionally substituted with one or more moieties which are, independently:
  - i. halogen, and when selected to be halogen is preferably —F or —Cl;
  - ii. N($R^{1d}$)$_2$, wherein "$R^{1d}$" is, independently for each occurrence, —H or lower alkyl;
  - iii. lower alkyl;
  - iv. lower alkoxy;
  - v. an aryl moiety, as defined herein, comprising up to 6 ring carbon atoms, wherein the aryl ring of said moiety is optionally substituted with up to 3 substituents which are independently for each occurrence: (1) —CN; (2) —OH; (3) halogen, preferably —F or —Br; (4) cyclic-, branched-, or linear-alkyl of up to 4 carbon atoms, which alkyl moiety is optionally substituted with: —OH; —CN; halogen; or N($R^{2d}$)$_2$, wherein "$R^{2d}$" is, independently for each occurrence, —H or lower alkyl; (5) —N($R^{3d}$)$_2$, wherein "$R^{3d}$" is, independently for each occurrence, —H or lower alkyl; (6) cyclic-, branched-, or linear-alkoxy of up to 4 carbon atoms; (7) a heterocycle moiety, as defined herein, comprising up to 5 carbon atoms and one or more heteroatoms which are N, O, or S; or
  - vi. a heteroaryl moiety, as defined herein, comprising up to 4 carbon atoms and at least one heteroatom, preferably said heteroaryl moiety is a 5-member heterocycle comprising at least one heteroatom which is N, S, or O, wherein said heteroaryl moiety is optionally substituted with one or more substituents which are independently: (a) —CN; (b) —OH; (c) halogen, preferably —F or —Br; (d) cyclic-, branched-, or linear-alkyl of up to 4 carbon atoms, which alkyl moiety is optionally substituted with: —OH; —CN; halogen; or N(R$^{4d}$)$_2$, wherein "R$^{4d}$" is, independently for each occurrence, —H or lower alkyl; or (e) cyclic-, branched-, or linear-alkoxy of up to 4 carbon atoms; or vii. —OH, with the proviso that "—OH" is not selected as a substituent on a carbon atom bonded adjacent to the nitrogen atom;

(c) an aryl moiety, as defined herein, comprising up to 6 ring carbon atoms, wherein the aryl ring of said moiety is optionally substituted with up to 3 substituents which are independently for each occurrence: (1) —CN; (2) —OH; (3) halogen, preferably —F or —Br; (4) cyclic-, branched-, or linear-alkyl of up to 4 carbon atoms, which alkyl moiety is optionally substituted with: —OH; —CN; halogen; or N(R$^{5d}$)$_2$, wherein "R$^{5d}$" is, independently for each occurrence, —H or lower alkyl; (5) —N(R$^{6d}$)$_2$, wherein "R$^{6d}$" is, independently for each occurrence, —H or lower alkyl; (6) cyclic-, branched-, or linear-alkoxy of up to 4 carbon atoms; (7) alkyl-thiol-moiety of up to 4 carbon atoms, and when selected to be a thiol moiety is preferably H$_3$C—S—; (8) alkyl-sulfonyl moiety of up to 4 carbon atoms, and when selected to be a sulfonyl moiety is preferably H$_3$C—S(O)$_2$—; or (9) a heterocycle moiety, as defined herein, comprising up to 5 carbon atoms and one or more heteroatoms which are N, O, or S;

(d) a heteroaryl moiety, as defined herein, comprising up to 4 carbon atoms and at least one heteroatom, preferably said heteroaryl moiety is a 5-member heterocycle comprising at least one heteroatom which is N, S, or O, wherein said heteroaryl moiety is optionally substituted with one or more substituents which are independently: (a) —CN; (b) —OH; (c) halogen, preferably —F or —Br; (d) cyclic-, branched-, or linear-alkyl of up to 4 carbon atoms, which alkyl moiety is optionally substituted with: —OH; —CN; halogen; or N(R$^{7d}$)$_2$, wherein "R$^{7d}$" is, independently for each occurrence, —H or lower alkyl; or (e) cyclic-, branched-, or linear-alkoxy of up to 4 carbon atoms; or (e) a heterocycle moiety, as defined herein, comprising up to 5 carbon atoms and one or more heteroatoms which are N, O, or S;

R$^1$ and R$^2$ are independently for each occurrence: (a) hydrogen; (b) halogen, preferable Cl or F; (c) —CN; or (d) C$_{1-6}$-alkyl, wherein one or more of the carbon atoms is partially or fully substituted with halogen or C$_{1-4}$-alkyl; and R$^3$ is (i) a moiety of Formula S1 or S2:

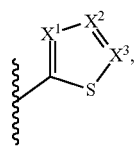

Formula S1

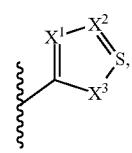

Formula S2 wherein one or two of X$^1$ to X$^3$ is —N= and the others are [=CR$^6$—], wherein "R$^6$" is:

(a) —H;

(b) an alkyl moiety which is —C$_{1-6}$-linear alkyl or —C$_{3-6}$-branched alkyl, which alkyl moiety is optionally substituted with one or more moieties which are independently for each occurrence: (a) halogen, preferably —F, and when halogen substitution is selected to provide a perfluorinated alkyl moiety, preferably the perfluorinated alkyl moiety provided is —CF$_3$; or (b) —C$_{3-6}$-cycloalkyl, which is optionally substituted;

(c) C$_{1-6}$-linear alkyl-C(O)—O—, C$_{3-6}$-branched alkyl-C(O)—O— or C$_{3-6}$-cycloalkyl-C(O)—O—;

(d) —C$_{3-6}$-cycloalkyl optionally substituted with —F or C$_{1-6}$-linear alkyl; or (e) halogen, and when selected to be a halogen, "R$^6$" is preferably —Cl or —F; or (ii) a moiety of Formula S3:

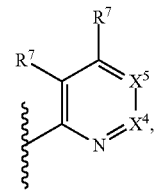

Formula S3 wherein:

"X$^4$" and "X$^5$" are independently [=N-] or [=CR$^7$—]; and

"R$^7$" is independently for each occurrence —H or —F, wherein no more than two "R$^7$" present in the moiety of S3 are selected to be "—F".

In some embodiments, preferably "A$^1$" is selected to be —[CR$^{10a}$R$^{11a}$]$_p$—CH$_2$—, thereby providing a substituent of Formula B$^2$-a:

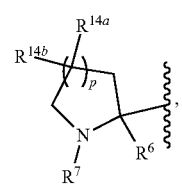

Formula B$^2$-a wherein:

"p" is 1 or 2;

one of "R$^{14a}$" or "R$^{14b}$" is selected to be —OH and the other occurrences of "R$^{14a}$" and "R$^{14b}$" are independently for each occurrence;

(a) —H;

(b) an aryl moiety which is optionally substituted on one or more ring carbon atoms with —OH or lower alkoxy;

(c) cyclic-, branched- or linear-alkyl moiety of up to 6 carbon atoms, which alkyl moiety is optionally substituted with one or more substituents which are, independently: (i) halogen; (ii) —OH; (iii) an aryl moiety which is optionally substituted with one or more substituents which are: (1) lower-alkoxy; (2) —N(R$^{1j}$)$_2$, wherein "R$^{1j}$" is, independently for each occurrence —H or lower alkyl; or (3) —OH; (iv) a heteroaryl moiety comprising up to 5 ring carbon atoms and at least one nitrogen heteroatom, which moiety is optionally substituted on one or more ring carbon atoms with a substituent which is, independently, —OH or lower alkoxy; or (v) heterocycloalkyl moiety comprising up to 6 carbon atoms and one or more heteroatoms selected from O, S, or N; or (d) —N($R^{1j}$)$_2$, wherein "$R^{1j}$" is, independently for each occurrence: —H or lower alkyl; and "$R^6$" is:

(a) —H;

(b) a branched-, cyclic- or linear-alkyl of up to 6 carbon atoms which is optionally substituted with one or more substituents which are, independently for each occurrence:
  (i) halogen;
  (ii) N($R^{1k}$)$_2$, wherein is, independently for each occurrence, —H or lower alkyl;
  (iii) lower alkoxy;
  (iv) an aryl moiety comprising up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N($R^{2k}$)$_2$, wherein "$R^{2k}$" is, independently for each occurrence, —H or lower alkyl; (5) —N($R^{3k}$)$_2$, wherein "$R^{3k}$" is, independently for each occurrence, —H or lower alkyl;
  (v) a heteroaryl moiety comprising up to 4 carbon atoms and at least one heteroatom, wherein said heteroaryl moiety is optionally substituted with one or more substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N($R^{4k}$)$_2$, wherein "$R^{4k}$" is, independently for each occurrence, —H or lower alkyl; (5) —N($R^{5k}$)$_2$, wherein "$R^{5k}$" is, independently for each occurrence, —H or lower alkyl; or
  (vi) a heterocycloalkyl moiety comprising one or more heteroatoms which are N, O, or S;

(c) an aryl moiety, as defined herein, wherein the aryl ring of said moiety is optionally substituted with up to 3 substituents which are independently for each occurrence: (i) —CN; (ii) —OH; (iii) halogen; (iv) cyclic-, branched-, or linear-alkyl of up to 4 carbon atoms, which alkyl moiety is optionally substituted with: (1) —OH; (2) —CN; (3) halogen; or (4) —N($R^{6k}$)$_2$, wherein "$R^{6k}$" is, independently for each occurrence, —H or lower alkyl; (v) —N($R^{7k}$)$_2$, wherein "$R^{7k}$" is, independently for each occurrence, —H or lower alkyl; (vi) cyclic-, branched-, or linear-alkoxy of up to 4 carbon atoms;

(d) a heteroaryl moiety, wherein said heteroaryl moiety comprises up to 5 ring carbon atoms and at least one heteroatom which is N, S, or O, and wherein said heteroaryl moiety is optionally substituted on one or more ring carbon atoms with a substituent which is independently for each occurrence: (i) —CN; (ii) —OH; (iii) halogen; (iv) cyclic-, branched-, or linear-alkyl of up to 4 carbon atoms, which alkyl moiety is optionally substituted with one or more substituents which are independently: (1) —OH; (2) —CN; (3) halogen; or (4) —N($R^{8k}$)$_2$, wherein "$R^{8k}$" is, independently for each occurrence, —H or lower alkyl; or (v) cyclic-, branched-, or linear-alkoxy of up to 4 carbon atoms; or (e) a heterocycloalkyl moiety comprising up to 5 carbon atoms and one or more heteroatoms which are N, O, or S; and "$R^7$" is:

(a) —H;

(b) an cyclic-, branched-, or linear-alkyl moiety of up to 7 carbon atoms which is optionally substituted with one or more moieties which are, independently:
  (i) halogen, and when selected to be halogen is preferably —F or —Cl;
  (ii) N($R^{1L}$)$_2$, wherein "$R^{1L}$" is, independently for each occurrence: (1) —H; or (2) lower alkyl;
  (iii) lower alkyl;
  (iv) lower alkoxy;
  (v) an aryl moiety, as defined herein, comprising up to 6 ring carbon atoms, wherein the aryl ring of said moiety is optionally substituted with up to 3 substituents which are independently for each occurrence: (1) —CN; (2) —OH; (3) halogen, preferably —F or —Br; (4) —N($R^{3L}$)$_2$, wherein "$R^{3L}$" is, independently for each occurrence: (I) —H; or (II) lower alkyl; (5) cyclic-, branched-, or linear-alkyl of up to 4 carbon atoms, which alkyl moiety is optionally substituted with: (I) —OH; (II) —CN; (III) halogen; or (IV) —N($R^{2L}$)$_2$, wherein "$R^{2L}$" is, independently for each occurrence: —H; or lower alkyl; (6) cyclic-, branched-, or linear-alkoxy of up to 4 carbon atoms; (7) a heterocycle moiety, as defined herein, comprising up to 5 carbon atoms and one or more heteroatoms which are N, O, or S;
  (vi) a heteroaryl moiety, as defined herein, comprising up to 4 carbon atoms and at least one heteroatom, preferably said heteroaryl moiety is a 5-member heterocycle comprising at least one heteroatom which is N, S, or O, wherein said heteroaryl moiety is optionally substituted with one or more substituents which are independently: (1) —CN; (2) —OH; (3) halogen, preferably: (I) —F; or (II) —Br; (4) cyclic-, branched-, or linear-alkyl of up to 4 carbon atoms, which alkyl moiety is optionally substituted with: (I) —OH; (II) —CN; (III) halogen; or (IV) —N($R^{4d}$)$_2$, wherein "$R^{4d}$" is, independently for each occurrence: —H; or lower alkyl; or (5) cyclic-, branched-, or linear-alkoxy of up to 4 carbon atoms; or
  (vii) —OH, with the proviso that "—OH" is not selected as a substituent on a carbon atom bonded adjacent to the nitrogen atom;

(c) an aryl moiety, as defined herein, comprising up to 6 ring carbon atoms, wherein the aryl ring of said moiety is optionally substituted with up to 3 substituents which are independently for each occurrence: (i) —CN; (ii) —OH; (iii) halogen, preferably —F or —Br; (iv) cyclic-, branched-, or linear-alkyl of up to 4 carbon atoms, which alkyl moiety is optionally substituted with one or more substituents which are independently: (1) —OH; (2) —CN; (3) halogen; or (4) —N($R^{5d}$)$_2$, wherein "$R^{5d}$" is, independently for each occurrence: (I) —H; or (II) lower alkyl; (5) —N($R^{6d}$)$_2$, wherein "$R^{6d}$" is, independently for each occurrence: —H; or lower alkyl; (6) cyclic-, branched-, or linear-alkoxy of up to 4 carbon atoms; (7) alkyl-thiol-moiety of up to 4 carbon atoms, and when selected to be a thiol moiety is preferably H$_3$C—S—; (8) alkyl-sulfonyl moiety of up to 4 carbon atoms, and when selected to be a sulfonyl moiety is preferably H₃C—S(O)₂—; or (9) a heterocycle moiety, as defined herein, comprising up to 5 carbon atoms and one or more heteroatoms which are N, O, or S;

(d) a heteroaryl moiety, as defined herein, comprising up to 4 carbon atoms and at least one heteroatom, preferably said heteroaryl moiety is a 5-member heterocycle comprising at least one heteroatom which is N, S, or O, wherein said heteroaryl moiety is optionally substituted with one or more substituents which are independently: (i) —CN; (ii) —OH; (iii) halogen, preferably —F or —Br; (iv) cyclic-, branched-, or linear-alkyl of up to 4 carbon atoms, which alkyl moiety is optionally substituted with: (1) —OH; (2) —CN; (3) halogen; or (4) —N(R$^{7d}$)₂, wherein "R$^{7d}$" is, independently for each occurrence: (I) —H; or (II) lower alkyl; or (5) cyclic-, branched-, or linear-alkoxy of up to 4 carbon atoms; or (e) a heterocycle moiety, as defined herein, comprising up to 5 carbon atoms and one or more heteroatoms which are N, O, or S.

In some embodiments, preferable, one occurrence of R$^{14a}$" or "R$^{14b}$" is —OH, and the other occurrences of "R$^{14a}$" and "R$^{14b}$" are independently for each occurrence: (a) —H; or (b) cyclic-, branched-, or linear-alkyl of up to 6 carbon atoms, which alkyl moiety is optionally substituted with one or more substituents which are, independently: (i) —OH; (ii) halogen; or (iii) —N(R$^{1ba}$)₂, wherein "R$^{1ba}$" is, independently: (1) —H; or (2) lower-alkyl;

In some embodiments it is preferred for R³ to be a moiety of Formula S1a:

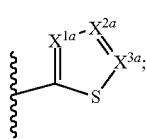

Formula S1a wherein: one of X$^{1a}$ to X$^{3a}$ is —N═ and the others are —CR⁸═, where —R⁸ is independently for each occurrence: (i) —H; (ii) lower-alkyl; or (iii) a halogen, and when a halogen R⁸ is preferably —Cl or —F. In some embodiments where R³ is a moiety of Formula S1 it is preferred for X¹ to be —N═ and X² and X³ to be —CR⁸═, wherein —CR⁸═ is as defined above, more preferably, X² is —CH═ and X³ is —CR⁸═, wherein —CR⁸═ is as defined above.

In some embodiments it is preferred for R³ to be a moiety of Formula S1b:

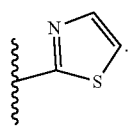

Formula S1b

In some embodiments, a compound of the invention is preferably:

4-((((2S,4S)-2-benzyl-4-hydroxypyrrolidin-2-yl)methyl) amino)-5-chloro-2-fluoro-N-(thiazol-2-yl)benzenesulfonamide;

5-chloro-4-((((2S,4S)-2-(cyclobutylmethyl)-4-hydroxypyrrolidin-2-yl)methyl)amino)-2-fluoro-N-(thiazol-2-yl)benzenesulfonamide;

5-chloro-2-fluoro-4-((((2S,4S)-4-hydroxy-2-phenethylpyrrolidin-2-yl)methyl)amino)-N-(thiazol-2-yl)benzenesulfonamide;

4-((((2S,4S)-2-(4-bromobenzyl)-4-hydroxypyrrolidin-2-yl) methyl)amino)-5-chloro-2-fluoro-N-(thiazol-2-yl)benzenesulfonamide;

4-((((2S,4S)-2-(4-(aminomethyl)benzyl)-4-hydroxypyrrolidin-2-yl) methyl)amino)-5-chloro-2-fluoro-N-(thiazol-2-yl)benzenesulfonamide;

5-chloro-2-fluoro-4-((((2S,4S)-4-hydroxy-2-(3-phenylpropyl)pyrrolidin-2-yl)methyl)amino)-N-(thiazol-2-yl)benzenesulfonamide;

4-((((2S,4S)-2-(3-(aminomethyl)benzyl)-4-hydroxypyrrolidin-2-yl)methyl)amino)-5-chloro-2-fluoro-N-(thiazol-2-yl)benzenesulfonamide;

4-((((2S,4S)-2-(3-bromobenzyl)-4-hydroxypyrrolidin-2-yl) methyl)amino)-5-chloro-2-fluoro-N-(thiazol-2-yl)benzenesulfonamide;

5-chloro-2-fluoro-4-((((2S,4S)-4-hydroxy-2-(3-methoxybenzyl)pyrrolidin-2-yl)methyl)amino)-N-(thiazol-2-yl) benzenesulfonamide;

5-chloro-2-fluoro-4-((((2S,4S)-4-hydroxy-2-(3-methylbenzyl)pyrrolidin-2-yl)methyl)amino)-N-(thiazol-2-yl)benzenesulfonamide;

5-chloro-2-fluoro-4-((((2S,4S)-2-(3-fluorobenzyl)-4-hydroxypyrrolidin-2-yl)methyl)amino)-N-(thiazol-2-yl) benzenesulfonamide;

5-chloro-4-((((2S,4S)-2-(3-cyanobenzyl)-4-hydroxypyrrolidin-2-yl)methyl)amino)-2-fluoro-N-(thiazol-2-yl)benzenesulfonamide;

5-chloro-4-((((2S,4S)-2-(3,3-dimethylbutyl)-4-hydroxypyrrolidin-2-yl)methyl)amino)-2-fluoro-N-(thiazol-2-yl)benzenesulfonamide;

5-chloro-2-fluoro-4-((((2S,4S)-4-hydroxy-2-(4-(pyridin-2-yl)benzyl)pyrrolidin-2-yl)methyl)amino)-N-(thiazol-2-yl)benzenesulfonamide;

5-chloro-2-fluoro-4-((((2S,4S)-4-hydroxy-2-(4-(oxazol-2-yl)benzyl)pyrrolidin-2-yl)methyl)amino)-N-(thiazol-2-yl)benzenesulfonamide;

4-((((2S,4S)-2-(4-(1H-pyrazol-5-yl)benzyl)-4-hydroxypyrrolidin-2-yl) methyl)amino)-5-chloro-2-fluoro-N-(thiazol-2-yl)benzenesulfonamide; or 5-chloro-4-((((2S,4S)-2-(4-cyanobenzyl)-4-hydroxypyrrolidin-2-yl)methyl)amino)-2-fluoro-N-(thiazol-2-yl)benzenesulfonamide, or a pharmaceutically acceptable salt of any thereof.

In one aspect the invention provides a pharmaceutical composition comprising at least one compound of Formula A, or a salt thereof, and at least one pharmaceutically acceptable excipient adapted for administration to a patient via any pharmaceutically acceptable route, including dosage forms for oral, intravenous, subcutaneous, transcutaneous, intramuscular, intradermal, transmucosal, or intramucosal routes of administration.

In one aspect this invention provides also a pharmaceutical composition comprising a pharmaceutical carrier, an effective amount of at least one compound of Formula A, or a salt thereof, an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug), and a pharmaceutically acceptable carrier.

In one aspect the invention provides also a method of treatment, management, alleviation or amelioration of conditions or disease states which can be treated, managed, alleviated or ameliorated by specific blocking of Nav 1.7 channel activity, the method comprising administering to a patient in need thereof a composition comprising at least one compound of Formula A, or a salt thereof, in an amount providing a serum level of at least one said compound sufficient to effect said treatment, management, alleviation or amelioration of said conditions or disease states. Preferably the condition or disease state to be treated, managed, alleviated or ameliorated is a chronic pain disorder.

DETAILED DESCRIPTION OF THE INVENTION

As mentioned above, the invention provides compounds believed to have selective activity as $Na_v$ 1.7 sodium ion channel blockers which have the structure of Formula A, or a salt thereof:

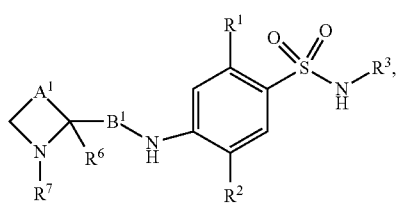

Formula A wherein "$A^1$", "$B^1$", "$R^1$", "$R^2$", "$R^3$", "$R^6$", and "$R^7$" are as defined herein above.

As used herein, unless otherwise specified, the term "$Na_v$ 1.7 blocker (equivalently, Nav 1.7 blocker") means a compound of the invention exhibiting a potency ($IC_{50}$) of less than about 2 μM when assayed in accordance with IonWorks® assay technique described herein. Preferred compounds exhibit at least 10-fold selectivity for $Na_v$ 1.7 sodium channels over $Na_v$ 1.5 sodium channels, more preferably at least 100-fold selectivity for $Na_v$ 1.7 sodium channels over $Na_v$ 1.5 sodium channels when functional potency for each channel are compared using the IonWorks® assay technique described herein.

Compounds of the invention and formulations comprising compounds of the invention are believed to be useful in providing treatment, management, alleviation or amelioration of conditions or disease states which can be treated, managed, alleviated or ameliorated by specific blocking of Nav 1.7 channel activity. Examples of disease states which can be desirably affected using such therapy include, but are not limited to, blocking neuropathic pain, for example, postherpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias, pruritis and cough.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

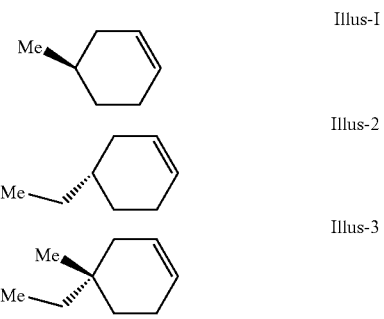

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one"; "concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration presented in the substrate, and that the substitution ultimate provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated substituents for the specified substrate can be present on the substrate in a bonding position normally occupied by the default substituent normally occupying that position. For example, a default substituent on the carbon atoms of an alkyl moiety is a hydrogen atom, an optional substituent can replace the default substituent.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, an "acyl" substituent may be equivalently described herein by the term "acyl", by typographical representations "R'—(C═O)—" or "R'—C(O)—", or by a structural representation:

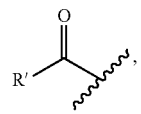

equally, with no differentiation implied using any or all of these representations;

"alkoxy" means a moiety of the structure: alkyl-O— (i.e., the bond to the substrate moiety is through the oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". The term "alkyl" is further defined by "Linear", "Branched" or "Cyclic. Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear-alkyl" includes alkyl moieties which comprise a hydrocarbon chain with no aliphatic hydrocarbon "branches" appended to it, although other substituents may replace a CH bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a mono- or bicyclo-cyclic aliphatic moiety comprising at least 3 carbon atoms (the minimum number necessary to provide a monocyclic moiety) up to the maximum number of specified carbon atoms, generally 8 for a monocyclic moiety and 10 for a bicyclic moiety. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to 20 carbon atoms which may optionally be substituted as defined herein for "alkyl" generally. Suitable multicyclic cycloalkyls are, for example, but are not limited to: 1-decalin; norbornyl; adamantly; and the like;

As used herein, when the term "alkyl" is modified by "substituted" or "optionally substituted", it means that one or more C—H bonds in the alkyl moiety group is substituted, or optionally may be substituted, by a substituent bonded to the alkyl substrate which is called out in defining the moiety.

"lower alkyl" means a linear, branched, or cycloalkyl moiety comprising up to 6 carbon atoms; non-limiting examples of suitable lower alkyl groups include methyl, ethyl, n-propyl, isopropyl, cyclopropyl, n-butyl, t-butyl, cyclobutyl, n-pentyl, isopentyl, neopentyl, cyclopentyl, n-hexyl, cyclohexyl and the like;

"lower alkoxy" means [R—O-] where "R" is a linear or branched alkyl moiety comprising up to 6 carbon atoms; examples of suitable lower alkoxy groups include, but are not limited to, methoxy, ethoxy, n-propoxy, isopropoxy, cyclopropoxy, n-butoxy, t-butoxy, cyclobutoxy, n-pentoxy, isopentoxy, neopentoxy, cyclopentoxy, methoxy-cyclopentane, and the like;

"lower cyclo-alkoxy" means [R—O-] where "R" is a cycloalkyl moiety comprising up to 6 carbon atoms;

"aryl" (sometimes abbreviated "ar") means an aromatic monocyclic or multicyclic ring system comprising 6 to 14 carbon atoms (denoted herein also as "$C_{6-14}$-aryl"), preferably 6 to 10 carbon atoms ("$C_{6-10}$-aryl"); Non-limiting examples of suitable aryl groups include phenyl

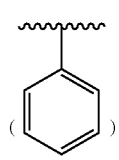

and naphthyl

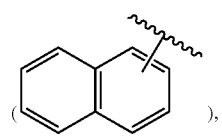

wherein bonding can be through any of the carbons in the aromatic ring, and wherein any ring carbon atoms not participating in a bond to the substrate may have bonded to it a substituent other than —H, independently selected in each instance from an enumerated list of substituents defined with the term;

"heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-,

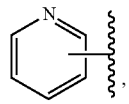

thiophenyl-

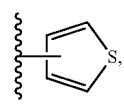

furanyl-,

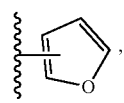

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure:

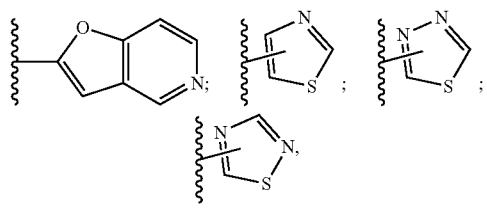

and the like, (unless otherwise indicated, such moieties may be bonded to the substrate through any available ring atom that results in a stable bonding arrangement);

"heteroaryloxy" means a heteroaryl moiety which is bonded to the substrate through an oxygen linker;

"heterocyclyl" (or heterocycloalkyl) means a non-aromatic saturated monocyclic or multicyclic ring system comprising 3 to 10 ring atoms, preferably 5 to 10 ring atoms, in which one or more of the atoms in the ring system is an element other than carbon, for example nitrogen (e.g. piperidyl- or pyrrolidinyl), oxygen (e.g. furanyl and tetrahydropyranyl) or sulfur (e.g. tetrahydrothiopheneyl and tetrahydrothiopyranyl); and wherein the heteroatoms can be alone or in combination provided that the moiety does not contain adjacent oxygen and/or sulfur atoms present in the ring system; preferred heterocyclyl moieties contain 5 to 6 ring atoms; the prefix aza, oxa or thia before the heterocyclyl root name means that at least one nitrogen, oxygen or sulfur atom, respectively, is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide ($SO_2$); non-limiting examples of suitable monocyclic heterocyclyl rings include piperidyl, pyrrolidinyl, piperazinyl, morpholinyl

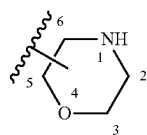

(where unless otherwise noted the moiety is bonded to the substrate through any of ring carbon atoms C2, C3, C5, or C6), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

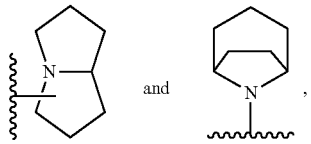

and the like.

"aryloxy" means an aryl-O— group (i.e., the moiety is bonded to a substrate through the ether oxygen) wherein the aryl group is as defined above; non-limiting examples of suitable aryloxy groups include phenoxy and naphthoxy;

the term the terms "sulfinyl" means (—SO—), "sulfonyl" means (—$S(O_2)$—), and the term "thio" means (—S—), and in combination with any other substituent terms, mean the same thing, thus, for example: "arylsulfinyl" means an aryl-S(O)— group; "arylsulfonyl" means an aryl-$S(O_2)$— group; and "arylthio" means an aryl-S— group (i.e., the bond of the first-named substituent is to the substrate through the sulfur atom in each case) wherein aryl is unsubstituted or substituted as previously defined;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$;

"tetrahydropyranyl" moiety means a 6-member cyclic ether of the formula:

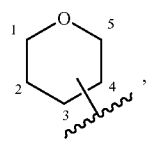

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate can optionally be occupied by specified or optional substituents;

"piperidinyl" means:

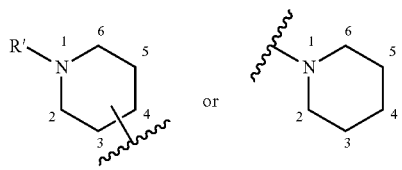

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), and wherein any of the bonding positions on the nitrogen atom or on carbon atoms 2 to 6 not participating in a bond to the substrate and normally occupied by a hydrogen atom can be bonded to a specified or optional substituent, and wherein R', if present, is either —H or another specified substituent;

"pyridinyl" means:

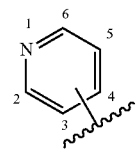

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, can optionally be occupied by a specified substituent;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

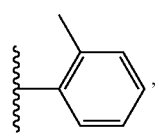

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

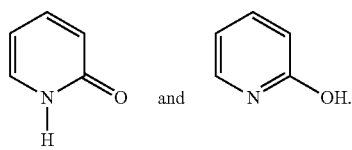 [SMILES: O=c1cccc[nH]1 ; "and" ; Oc1ccccn1]

In particular, compounds of the invention are presented herein having a portion of their structure represented by the structural drawing

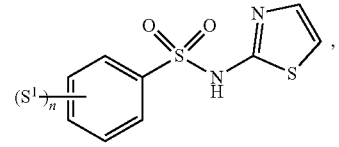

where $(S^1)n$ is one to five substituents on the aryl ring, the structural drawing representation is intended to include the tautomer:

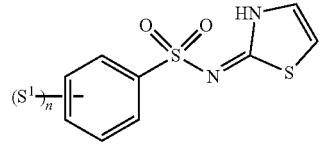

within the scope of the structures represented thereby.

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^{3}H$, $^{11}C$ and $^{14}C$) are recognized as being particularly useful in compound and/or substrate tissue distribution assays using a variety of known techniques. Tritiated (i.e., $^{3}H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

As mentioned above, in one aspect the invention provides pharmaceutical formulations (pharmaceutical compositions) suitable for use in selectively blocking Nav 1.7 sodium channels found in sensory and sympathetic neurons, comprising at least one compound of the invention (as defined herein, for example one or more compounds of Formula A, or a salt thereof) and at least one pharmaceutically acceptable carrier (described below). It will be appreciated that pharmaceutical formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below. Such formulations are believed to have utility in the treatment, management, amoleration or in providing therapy for diseases or conditions related to chronic or inflammatory neuropathic pain disorders, pruritic disorders and cough disorders.

In one aspect this invention provides also pharmaceutical compositions which comprise in addition to at least one pharmaceutically acceptable carrier and an effective amount of at least one compound of the invention (e.g, a compound of Formula A or a salt thereof), an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug), and a pharmaceutically acceptable carrier.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula A. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for injection, for example, an injectable solution or suspension adapted for subcutaneous injection (Sub-Q) or intramuscular administration (IM), for example, where the injectable solution or suspension may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastro-intestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

In some embodiments, for use in the preparation of a pharmaceutical formulation, preferably a compound of the invention is a compound of Formula A-a or a salt thereof:

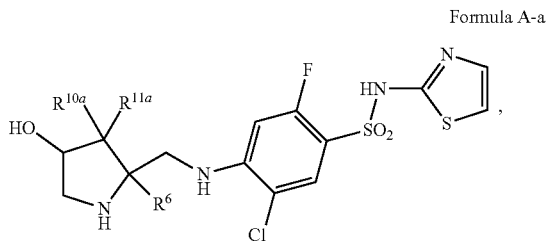

Formula A-a wherein: "$R^6$", "$R^{10a}$", and "$R^{11a}$" are as defined herein.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula A. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, MD Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for treatment, management, prevention, alleviation or amelioration of conditions or disease states which can be treated, managed, prevented, alleviated or ameliorated by specific blocking of Nav 1.7 channel activity, for example, Pruritic conditions, cough conditions, and blocking neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with cancer and chemotherapy, pain associated with HIV, and HIV treatment-induced neuropathy, nerve injury, root avulsions, painful traumatic mononeuropathy, painful polyneuropathy, erythromelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmenorrhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain.

In accordance with the present invention, treatment, alleviation, amelioration, or management of a disease state amenable to treatment by blocking $Na_v$ 1.7 channel activity, for example, one or more of the conditions or disease states mentioned above, comprises administering to a patient in need thereof an effective amount of one or more compounds of the invention, as defined herein, for example, a compound of Formula A or a pharmaceutically acceptable salt thereof. In some embodiments, as mentioned above, it is preferred for the compound of the invention to be present in a pharmaceutical formulation Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, NJ 07645-1742, USA), the Physician's Desk Reference, 56$^{th}$ Edition, 2002 (published by Medical Economics company, Inc. Montvale, NJ 07645-1742), or the Physician's Desk Reference, 57$^{th}$ Edition, 2003 (published by Thompson PDR, Montvale, NJ 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

In general, in what ever form administered, the dosage form administered will contain an amount of at least one compound of the invention, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment.

In one aspect this invention provides also a pharmaceutical composition comprising a pharmaceutical carrier, an effective amount of at least one compound of the invention, an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug), and a pharmaceutically acceptable carrier.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

As mentioned above, in one aspect the invention provides compounds having activity as Nav 1.7 sodium ion channel blockers which have the structure of Formula A, or a salt thereof:

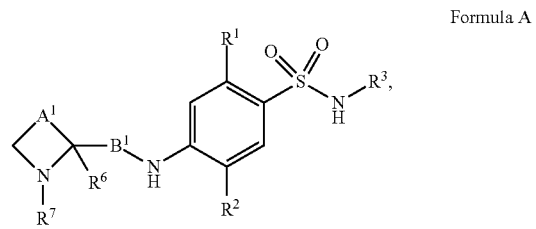

Formula A wherein "$A^1$", "$R^1$", "$R^2$", "$R^3$", "$R^6$", "$R^7$", and "$B^1$" are as defined herein above.

In some embodiments in compounds of Formula A, "$R^1$" is preferably —F. In some embodiments in compounds of Formula A, "$R^2$" is preferably —Cl.

In some embodiments of Formula A, "$R^3$" is preferably a moiety of the formula:

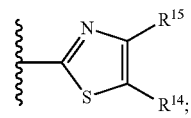

wherein one of "$R^{14}$" and "$R^{15}$" are —H and the other is: (i) —H; or (ii) halogen, preferably —F or —Cl.

In some embodiments in compounds of Formula A, "$B^1$" is preferably a moiety of the formula —$CR^4R^5$—, wherein one of "$R^4$" and "$R^5$" is —H and the other is: (i) —H; (ii) cyclic-, branched-, or linear-alkyl moiety of up to 6 carbon atoms, and when selected to be alkyl is preferably methyl, ethyl, n-propyl, cyclopropyl or isopropyl, which is optionally substituted with one or more substituents which are, independently:

(a) an aryl moiety;
(b) a heteroaryl moiety;
(c) halogen;
(d) —CN; or
(e) —N($R^{5aa}$)$_2$, wherein "$R^{5aa}$" is independently for each occurrence: (1) H; (2) linear-, branched, or cyclic-alkyl of up to 4 carbon atoms.

In some embodiments in compounds of Formula A where "$B^1$" is preferably selected to be a moiety of the formula "—$CR^4R^5$—", preferably both "$R^4$" and "$R^5$" are —H.

In some embodiments in compounds of Formula A, "$B^1$" is preferably a moiety of the formula —($CR^4R^5$)—$CH_2$—, wherein one of "$R^4$" and "$R^5$" is —H and the other is as defined above.

In some embodiments it is preferred for the compound of Formula A to be a compound of Formula A-b:

Formula A-b

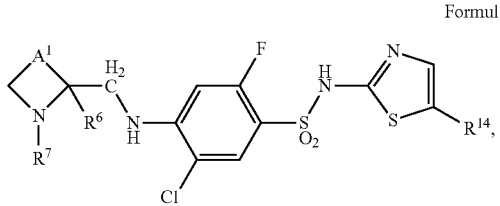

wherein:
R$^{14}$ is: (a) H; (b) halogen, preferably —F or —Cl; (c) cyclic-, branched-, or linear-alkyl of up to 6 carbon atoms, and in some embodiments preferably methyl; or (d) —C(O)—O-lower-alkyl; and
"A$^1$", R$^6$ and R$^7$ are as defined above for the compound of Formula A.

As mentioned above, in some embodiments, in compounds of Formulae A-a and Formula A-b, preferably "A$^1$" is selected to be —(CR$^{14b}$R$^{14a}$)$_p$—CH$_2$—, yielding a moiety of Formula B$^2$-a:

Formula B$^2$-a

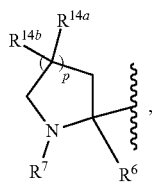

wherein "p", "R$^6$", R$^7$", "R$^{14a}$" and "R$^{14b}$" are defined above.

In some embodiments wherein the compound comprises a moiety of Formula B$^2$-a, preferably one occurrence of R$^{14a}$" or "R$^{14b}$" is —OH, and the other occurrences of "R$^{14a}$" and "R$^{14b}$" are independently for each occurrence: (a) —H; or (b) cyclic-, branched-, or linear-alkyl of up to 6 carbon atoms, which alkyl moiety is optionally substituted with one or more substituents which are, independently: (i) —OH; (ii) halogen; or (iii) —N(R$^{1ba}$)$_2$, wherein "R$^{1ba}$" is, independently: (1) —H; or (2) lower-alkyl In some embodiments wherein the compound comprises a moiety of Formula B$^2$-a, preferably: "p" is "1" and one of "R$^{14a}$" or "R$^{14b}$" is —H or —CH$_3$, and the other is —OH.

In some embodiments, in compounds of Formulae A-a and Formula A-b, it is preferred for "A$^1$" to be selected to be —(HC(OH)—CR$^{10a}$R$^{11a}$)—, yielding a moiety of Formula B$^2$-b:

Formula B$^2$-b

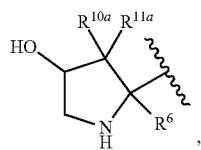

wherein "R$^{10a}$" and "R$^{11a}$" are independently for each occurrence:
(a) —H;
(b) an aryl moiety which is optionally substituted on one or more ring carbon atoms with —OH or lower alkoxy;
(c) cyclic-, branched- or linear-alkyl moiety of up to 6 carbon atoms, which alkyl moiety is optionally substituted with one or more substituents which are, independently: (i) halogen; (ii) —OH; (iii) an aryl moiety which is optionally substituted with one or more substituents which are: (1) lower-alkoxy; (2) —N(R$^{1j}$)$_2$, wherein "R$^{1j}$" is, independently for each occurrence —H or lower alkyl; or (3) —OH; (iv) a heteroaryl moiety comprising up to 5 ring carbon atoms and at least one nitrogen heteroatom, which moiety is optionally substituted on one or more ring carbon atoms with a substituent which is, independently, —OH or lower alkoxy; or (v) heterocycloalkyl comprising up to 6 carbon atoms and one or more heteroatoms selected from O, S, or N; or
(d) —N(R$^{1j}$)$_2$, wherein "R$^{1j}$" is, independently for each occurrence: —H or lower alkyl; and "R$^6$" is:
(a) —H;
(b) a branched-, cyclic- or linear-alkyl of up to 6 carbon atoms which is optionally substituted with one or more substituents which are, independently for each occurrence:
  (i) halogen;
  (ii) N(R$^{1k}$)$_2$, wherein "R$^{1k}$", is, independently for each occurrence, —H or lower alkyl;
  (iii) lower alkoxy;
  (iv) an aryl moiety comprising up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N(R$^{2k}$)$_2$, wherein "R$^{2k}$" is, independently for each occurrence, —H or lower alkyl; (5) —N(R$^{3k}$)$_2$, wherein "R$^{3k}$," is, independently for each occurrence, —H or lower alkyl;
  (v) a heteroaryl moiety comprising up to 4 carbon atoms and at least one heteroatom, wherein said heteroaryl moiety is optionally substituted with one or more substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N(R$^{4k}$)$_2$ wherein "R$^{4k}$," is, independently for each occurrence, —H or lower alkyl; (5) —N(R$^{5k}$)$_2$, wherein "R$^{5k}$" is, independently for each occurrence, —H or lower alkyl; or
  (vi) a heterocycloalkyl moiety comprising one or more heteroatoms which are N, O, or S;
(c) an aryl moiety, as defined herein, wherein the aryl ring of said moiety is optionally substituted with up to 3 substituents which are independently for each occurrence: (i) —CN; (ii) —OH; (iii) halogen; (iv) cyclic-, branched-, or linear-alkyl of up to 4 carbon atoms, which alkyl moiety is optionally substituted with: (1) —OH; (2) —CN; (3) halogen; or (4) —N(R$^{6k}$)$_2$, wherein "R$^{6k}$," is, independently for each occurrence, —H or lower alkyl; (v) —N(R$^{7k}$)$_2$, wherein "R$^{7k}$," is, independently for each occurrence, —H or lower alkyl;
(vi) cyclic-, branched-, or linear-alkoxy of up to 4 carbon atoms;
(d) a heteroaryl moiety, wherein said heteroaryl moiety comprises up to 5 ring carbon atoms and at least one heteroatom which is N, S, or O, and wherein said heteroaryl moiety is optionally substituted on one or more ring carbon atoms with a substituent which is independently for each occurrence: (i) —CN; (ii) —OH; (iii) halogen; (iv) cyclic-, branched-, or linear-alkyl of up to 4 carbon atoms, which alkyl moiety is optionally substituted with one or more substituents which are independently: (1) —OH; (2) —CN; (3) halogen; or (4) —N($R^{8k}$)$_2$, wherein "$R^{8k}$" is, independently for each occurrence, —H or lower alkyl; or (v) cyclic-, branched-, or linear-alkoxy of up to 4 carbon atoms; or
(e) a heterocycloalkyl moiety comprising up to 5 carbon atoms and one or more heteroatoms which are N, O, or S.

In some embodiments wherein the compound comprises a moiety of Formula $B^2$-b, preferably, "$R^{10a}$" and "$R^{11a}$" are independently —CH$_3$ or —H.

In the examples that follow certain of the exemplified compounds, or salts thereof, are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

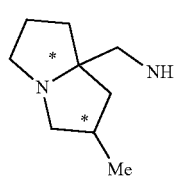

Def-1

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis -isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

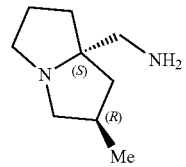

ABC-1

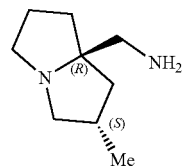

ABC-2

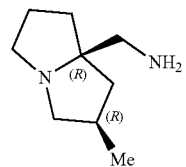

ABC-3

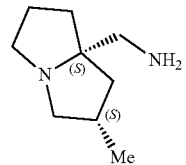

ABC-4

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine. In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds.

EXAMPLES

Examples of the preparation of compounds of the invention are shown next. In each of the Examples, the identity of the compounds prepared were confirmed by a variety of techniques. In all cases the compounds were analyzed by LC/MS or HPLC.

Where utilized, Prep HPLC was carried out on a Gilson 281 equipped with a Phenomenexd Synergi C18, 100 mm×21.2 mm×5 micron column. Conditions included a flow rate of 25 mL/min., eluted with a 0-40% acetonitrile/water eluent comprising 0.1% v/v TFA.

LC/MS determinations used either an Agilent YMC J'Sphere H-80 (3×50 mm) 5 µm column using mobile phase containing A: 0.10% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 µm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR was were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported.

High resolving power accurate mass measurements were acquired by use of a Bruker Daltonics 7T Fourier transform ion cyclotron resonance (FTICR) mass spectrometer. Samples were dissolved in acetonitrile:water:acetic acid (50:50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

EXAMPLES

Throughout the Examples section, the following abbreviations are used to indicate various reagents, substituents and solvents: AcOH=acetic acid; Boc$_2$O=di-tert-butyl carbonate; Bn=Benzyl; DABCO=1,4-diazabicyclo[2.2.2]octane; DAST=diethylaminosulfur trifluoride; DCM=dichloromethane; DEAD=diethylazodicarboxylate; DIPEA=diisopropylamine; DMB (2, 4-dimethoxybenzyl-); DMF=dimethylformamide; DMP=Dess-Martin Periodinane; DMS=dimethylsulfide; DMSO=dimethylsulfoxide; DPPA=diphenylphosphoryl azide; dppf=1,1'-bis(diphenylphosphino)ferrocene; EtOAc=ethyl acetate; EtOH=ethanol; HATU=1-[Bis(dimethylamino)methylene]-1H-1,2,3-triazolo[4,5-b]pyridinium-3-oxide-hexafluorophosphate; HMPA=hexamethylphosphoramide; HPLC=high-performance liquid chromatography; LDA=lithium diisopropylamide; LiHMDS=lithium bis(trimethylsilyl)amide; MeOH=methanol; MOMCl=methyl chloromethyl ether; MsCl=methanesulfonyl chloride; Pd/C=palladium on carbon; Pd$_2$(dba)$_3$=tris(dibenzylideneacetone)dipalladium(0); PE=petroleum ether; PMBCl=para-methoxybenzyl chloride; Prep-TLC=preparative thin layer chromatography; Py=pyridine; Selectfluor=1-(chloromethyl)-4-fluoro-1,4-diazoniabicyclo[2.2.2]octane ditetrafluoroborate; SFC=Supercritical Fluid Chromatography; TBS=tert-butyldimethylsilyl; THF=Tetrahydrofuran; TFA=trifluoroacetic acid; TFAA=trifluoroacetic acid anhydride; TsOH=para-toluenesulfonic acid; Xantphos=4,5-Bis(diphenylphosphino)-9,9-dimethylxanthene.

As illustrated in Scheme A, in general, compounds of the invention can be prepared by acylation of protected aryl-substituted or heteroaryl-substituted amines (A-2, PG=protecting group which is, for example, but not limited to, Boc, DMB, PMB, MOM) or unprotected aryl-substituted or heteroaryl-substituted amines (A-2, PG=H) with the appropriately functionalized sulfonyl chloride (A-1, LG=leaving group, which is, for example, but not limited to, F, Cl, Br) to afford intermediates of type A-3. Intermediates of type A-3 can undergo nucleophilic aromatic substitution reactions with amines (A-4) to afford final compounds of type A-5. Amines of type A-4 can be commercially available or synthesized as demonstrated in Schemes 1 to 5 and as generally illustrated in Scheme B.

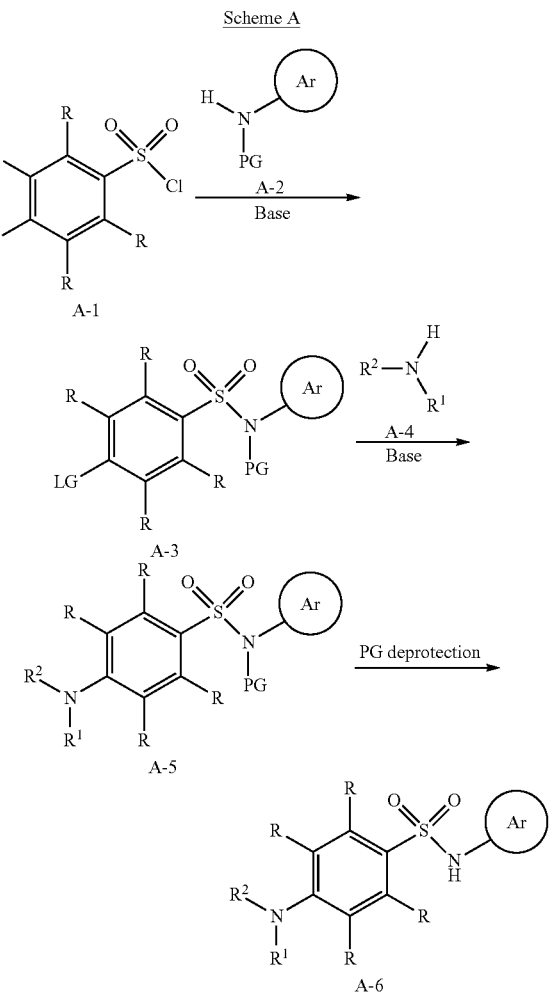

Scheme A

As illustrated in Scheme B, amines of type A-4 can be prepared by alkylation of protected azetidines, pyrrolidines, or piperidines (B-1, n=0, 1 or 2, PG can be, but not limited to, Boc, Cbz, Bn, or TBS on either the amine or alcohol) by reagents R—X under basic conditions to afford intermediates of type B-2. Intermediates of type B-2 can be reduced and then transformed into amines of type B-3 via reductive amination or Mitsunobu/deprotection of phthalimide intermediates.

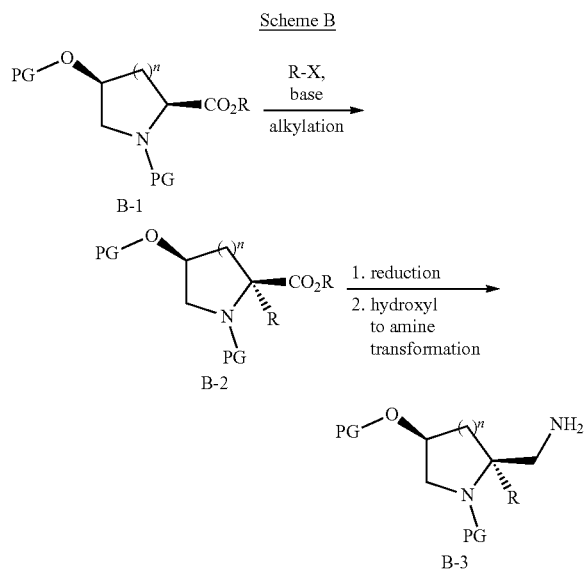

Example 1A 4-(((((2S,4S)-2-Benzyl-4-Hydroxypyrrolidin-2-Yl)Methyl)Amino)-5-Chloro-2-Fluoro-N-(Thiazol-2-Yl)Benzenesulfonamide (1-9, Method a)

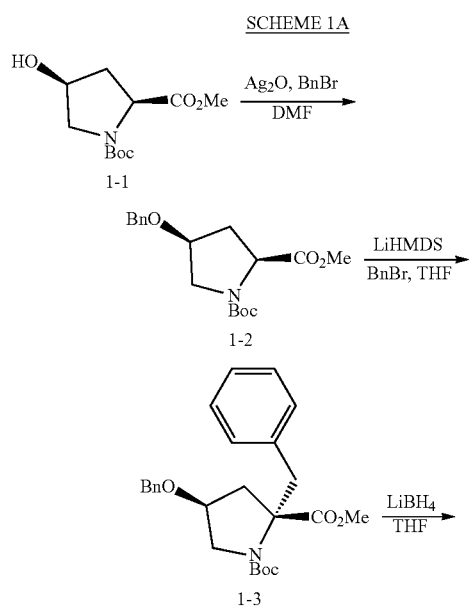

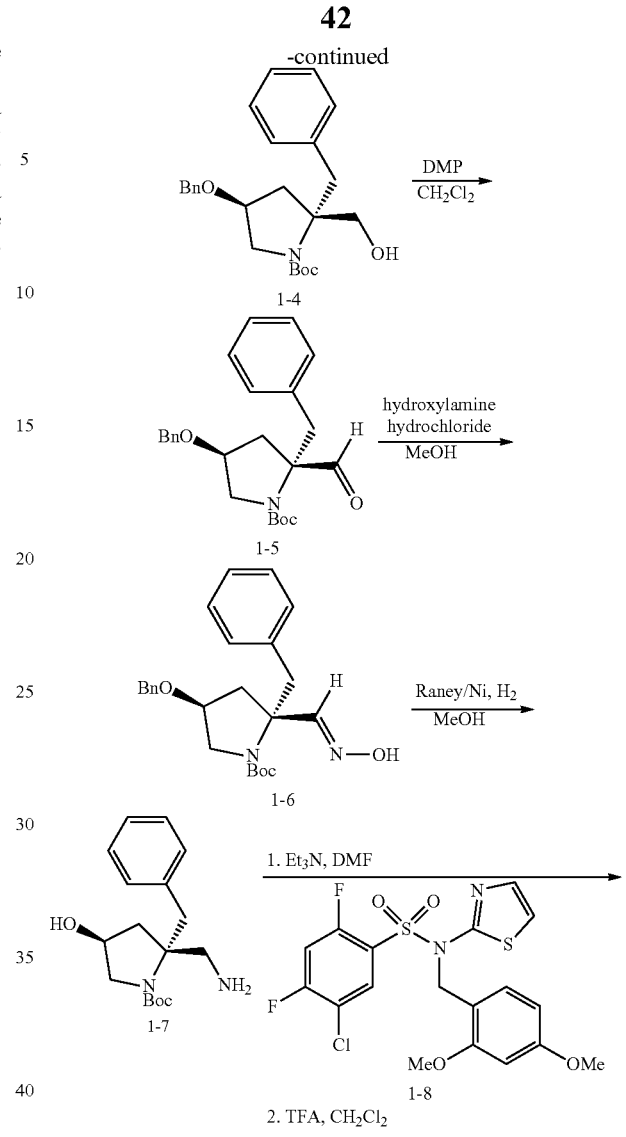

Preparation of (2S,4S)-1-Tert-Butyl 2-Methyl 4-(Benzyloxy)Pyrrolidine-1,2-Dicarboxylate To a solution of 1-1 (20 g, 82 mmol) in DMF (160 mL) at 0° C. was added (bromomethyl)benzene (30.7 g, 179 mmol), followed by Ag$_2$O (20.79 g, 90 mmol) and the suspension was stirred at room temperature for 15 hours. Then the reaction mixture was filtered and the solid was washed with EtOAc. The combined organic layers were diluted with water, extracted with EtOAc. The organics were washed with brine, dried over Na$_2$SO$_4$, filtered and concentrated. The mixture was purified by column chromatography (PE/EtOAc=20/1) to give 1-2.

$^1$H NMR (CDCl$_3$, 400 MHz,) δ 7.21-7.40 (m, 5H), 4.27-4.53 (m, 3H), 4.09-4.12 (m, 1H), 3.50-3.70 (m, 5H), 2.18-2.42 (m, 2H), 1.36-1.52 (m, 9H).

Preparation of (2S,4S)-1-Tert-Butyl 2-Methyl 2-Benzyl-4-(Benzyloxy)Pyrrolidine-1,2 Dicarboxylate (1-3)

To a solution of 1-2 (12 g, 35.8 mmol) in THF (40 mL) was added LiHMDS (1.0 M, 50 mL, 50 mmol) dropwise while keeping the temperature at −78° C. The solution was stirred for 1 h under nitrogen at this temperature. (Bromomethyl)benzene (9.18 g, 53.7 mmol) was added dropwise at −78° C. The solution was stirred at room temperature for 16 h. Saturated NH$_4$Cl was added to the reaction mixture, and the aqueous phase was extracted with EtOAc. The combined organic layers were washed with brine, dried over Na$_2$SO$_4$, filtered and concentrated to give crude product which was purified by column chromatography eluted with PE:EtOAc (20:1) to give 1-3.

$^1$H NMR (CDCl$_3$, 400 MHz) δ 7.20-7.34 (m, 6H), 7.04-7.20 (m, 4H), 4.13-4.25 (m, 2H), 3.74 (s, 3H), 3.48-3.57 (m, 1H), 3.24-3.42 (m, 2H), 2.80-3.02 (m, 2H), 2.09-2.30 (m, 2H), 1.48-1.55 (m, 9H).

Preparation of (2S,4S)-Tert-Butyl 2-Benzyl-4-(Benzyloxy)-2-(Hydroxymethyl)Pyrrolidine-1-Carboxylate (1-4)

To a solution of LiBH$_4$ (2.05 g, 94 mmol) in THF (200 mL) at 0° C. was added 1-3 (20 g, 47.0 mmol). The mixture was stirred at 25° C. for 18 h under N$_2$ atmosphere. TLC showed the starting material was not consumed completely, then additional LiBH$_4$ (1.02 g, 47 mmol) was added and the reaction was stirred for another 18 hours at 50° C. The reaction mixture was quenched with water (3 mL) and NaOH (aq. 15%, 3 mL), then water (9 mL). The mixture was dried over MgSO$_4$, filtered and concentrated. Then the mixture was purified by column chromatography (PE:EtOAc=10:1) to give 1-4.

$^1$H NMR (CDCl$_3$, 400 MHz) δ 7.24-7.38 (m, 8H), 7.10-7.17 (m, 2H), 5.16-5.26 (m, 1H), 4.33 (q, J=12.0 Hz, 2H), 3.91 (d, J=11.6 Hz, 1H), 3.74-3.81 (m, 1H), 3.50 (d, J=13.6 Hz, 1H), 3.28-3.42 (m, 2H), 3.04-3.14 (m, 1H), 2.78 (d, J=13.6 Hz, 1H), 2.16-2.21 (m, 3.6 Hz, 1H), 1.65-1.72 (m, 1H), 1.44-1.57 (m, 9H).

Preparation of (2S,4S)-Tert-Butyl 2-Benzyl-4-(Benzyloxy)-2-Formylpyrrolidine-1 Carboxylate (1-5)

To a solution of 1-4 (500 mg, 1.258 mmol) in CH$_2$Cl$_2$ (10 mL) was added Dess-Martin reagent (640 mg, 1.51 mmol) at 0° C. The solution was stirred for 1 h under N$_2$ at 25° C. The mixture was quenched with saturated NaHCO$_3$:Na$_2$SO$_3$ (1:1) and extracted with DCM. The organic layer was washed with brine and dried over MgSO$_4$, filtered and concentrated. The residue was purified by column chromatography (PE:EtOAc=10:1) to give the product of 1-5.

$^1$H NMR (CDCl$_3$, 400 MHz) δ 9.60-9.72 (m, 1H), 7.17-7.37 (m, 8H), 7.10-7.12 (m, 2H), 4.26-4.41 (m, 2H), 3.64-3.75 (m, 1H), 3.38-3.56 (m, 2H), 2.83-2.97 (m, 2H), 2.05-2.16 (m, 2H), 1.54 (m, 9H).

Preparation of (2S,4S)-Tert-Butyl 2-Benzyl-4-(Benzyloxy)-2-((E)-(Hydroxyimino)Methyl) Pyrrolidine-1-Carboxylate (1-6)

To a solution of 1-5 (1.7 g, 4.30 mmol) in EtOH (15 mL) was added sodium acetate (1.058 g, 12.90 mmol) and hydroxylamine hydrochloride (0.597 g, 8.60 mmol) at 25° C. Then the mixture was stirred at 25° C. for 18 h. The mixture was filtered and the filtrate was concentrated. Then the mixture was purified by column chromatography (PE: EtOAc=4:1) to give 1-6.

$^1$H NMR (CDCl$_3$, 400 MHz) δ 7.68-7.95 (m, 1H), 7.17-7.36 (m, 8H), 7.08-7.12 (m, 2H), 4.23-4.44 (m, 2H), 3.33-3.86 (m, 3H), 2.78-2.95 (m, 2H), 2.13-2.36 (m, 2H), 1.50-1.54 (m, 9H).

Preparation of (2S,4S)-Tert-Butyl 2-(Aminomethyl)-2-Benzyl-4-Hydroxypyrrolidine-1-Carboxylate (1-7)

To a solution of 1-6 (7 g, 17.05 mmol)) in MeOH (80 mL) was added Pd/C (1.5 g), then the mixture was stirred for 18 h under 50 psi of H$_2$ at 25° C. LCMS showed most 1-6 remained. Then the mixture was filtered and Raney Ni (1 g) was added to the filtrate. The mixture was stirred at 25° C. for 4 hours under 50 psi of H$_2$. Then the mixture was filtered and the filtrate was concentrated to give the crude 1-7.

Preparation of 4-((((2S,4S)-2-Benzyl-4-Hydroxypyrrolidin-2-Yl)Methyl)Amino)-5-Chloro-2-Fluoro-N-(Thiazol-2-Yl)Benzenesulfonamide (1-9)

To a solution of 1-7 (0.64 g, 2.089 mmol) and 1-8 (1.155 g, 2.507 mmol) in DMF (10 mL) was added triethylamine (1.057 g, 10.44 mmol) at 25° C. The mixture was stirred at 50° C. for 18 h under N$_2$ atmosphere. Then the reaction mixture was diluted with water, extracted with EtOAc. The organic layer was washed with brine, dried over MgSO$_4$ and concentrated. Then the mixture was purified by column chromatography (PE:EtOAc=3:1) to give (2S,4S)-tert-butyl 2-benzyl-2-(((2-chloro-4-(N-(2,4-dimethoxybenzyl)-N-(thiazol-2-yl)sulfamoyl)-5-fluorophenyl)amino)methyl)-4-hydroxypyrrolidine-1-carboxylate.

$^1$H NMR (CDCl$_3$, 400 MHz) δ 7.67-7.73 (m, 1H), 7.27-7.40 (m, 3H), 7.11-7.22 (m, 3H), 6.94 (d, J=4.0 Hz, 1H), 6.60-6.72 (m, 1H), 6.27-6.41 (m, 3H), 5.19 (br s, 2H), 3.83-4.01 (m, 2H), 3.75 (s, 6H), 3.55-3.73 (m, 1H), 3.26-3.48 (m, 2H), 2.81-2.93 (m, 1H), 2.64-2.79 (m, 1H), 2.37-2.47 (m, 1H), 1.83-2.01 (m, 1H), 1.38-1.50 (m, 9H). LRMS m/z (M+H) 747.1. found, 747.2 required.

To a solution of (2S,4S)-tert-butyl 2-benzyl-2-(((2-chloro-4-(N-(2,4-dimethoxybenzyl)-N-(thiazol-2-yl)sulfamoyl)-5-fluorophenyl)amino)methyl)-4-hydroxypyrrolidine-1-carboxylate (80 mg, 0.096 mmol) in DCM (2 mL) was added TFA (0.5 mL) at 25° C., and then the mixture was stirred at this temperature for 1 hour. The reaction mixture was concentrated. The residue was purified by prep-HPLC to give the desired product of 1-9.

$^1$H NMR (CD$_3$OD, 400 MHz) δ 7.75 (d, J=7.2 Hz, 1H), 7.30-7.41 (m, 5H), 7.12 (d, J=4.4 Hz, 1H), 6.74 (d, J=4.4 Hz, 1H), 6.58 (d, J=12.0 Hz, 1H), 4.57 (br s, 1H), 3.52-3.69 (m, 2H), 3.33-3.42 (m, 2H), 3.13-3.29 (m, 2H), 2.55 (dd, J=5.2, 14.4 Hz, 1H), 1.93 (d, J=14.4 Hz, 1H). LRMS m/z (M+H) 497.0. found, 497.1 required.

Example 1B 5-Chloro-4-((((2S,4S)-2-(Cyclobutylmethyl)-4-Hydroxypyrrolidin-2 Yl)Methyl)Amino)-2-Fluoro-N-(Thiazol-2-Yl)Benzenesulfonamide (1-15, Method B)

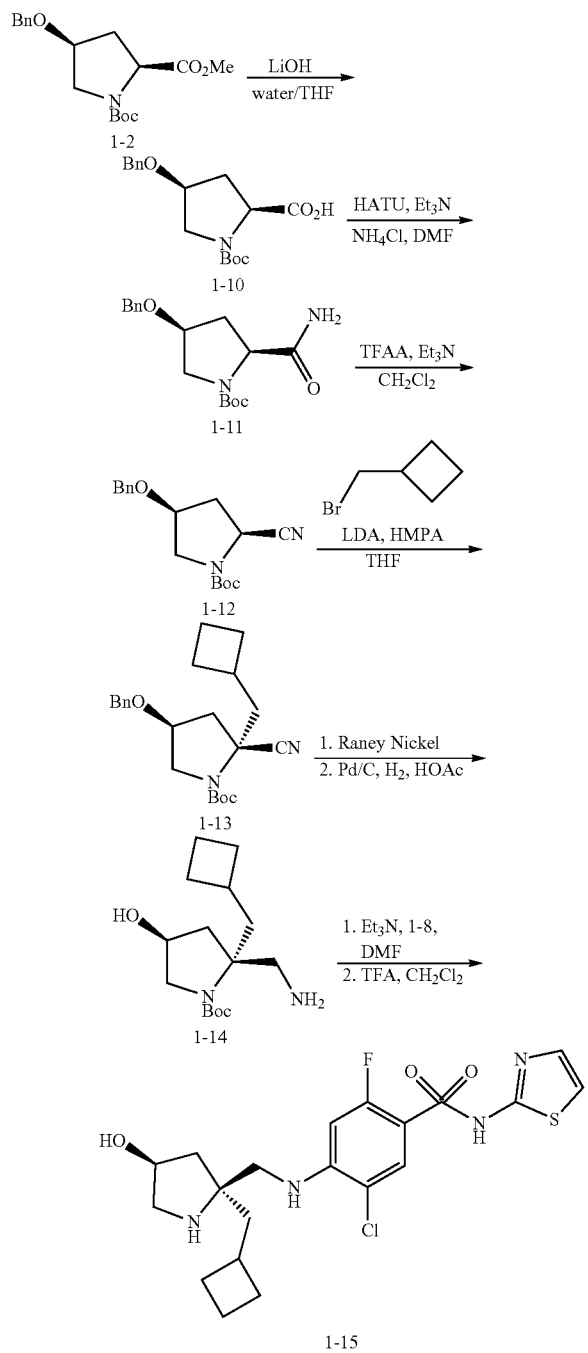

SCHEME 1B

Preparation of (2S,4S)-4-(Benzyloxy)-1-(Tert-Butoxycarbonyl)Pyrrolidine-2-Carboxylic Acid (1-10)

To a mixture of 1-2 (15 g, 44.7 mmol) in THF (150 mL) and H$_2$O (15 mL) was added LiOH (5.36 g, 224 mmol). The mixture was stirred at 15° C. for 12 h. After the reaction was complete, the mixture was concentrated. The residue was dissolved in water and citric acid was added into the mixture to adjust pH=3.0. The mixture was filtered to give 1-10, which was used in the next step without further purification.

Preparation of (2S,4S)-Tert-Butyl 4-(Benzyloxy)-2-Carbamoylpyrrolidine-1-Carboxylate (1-11)

To a mixture of 1-10 (14 g, 43.6 mmol), ammonium chloride (13.98 g, 261 mmol) and triethylamine (18.22 ml, 131 mmol) in DMF (100 mL) was added HATU (24.85 g, 65.3 mmol). The mixture was stirred at 25° C. for 12 h. After the reaction was complete, the mixture was diluted with EtOAc and filtered. The filtrate was concentrated. The residue was purified by chromatography (PE:EtOAc=3:1) to give 1-11.

$^1$H NMR (CDCl$_3$, 400 MHz) δ 7.24-7.34 (m, 5H), 5.66 (brs, 2H), 4.00-4.51 (m, 4H), 3.48-3.68 (m, 2H), 2.25-2.49 (m, 1H), 2.06-2.20 (m, 1H), 1.41 (s, 9H).

Preparation of (2S,4S)-Tert-Butyl 4-(Benzyloxy)-2-Cyanopyrrolidine-1-Carboxylate (1-12)

A solution of 1-11 (3 g, 9.36 mmol) in DCM (30 mL) and triethylamine (5.87 mL, 42.1 mmol) was cooled to 0° C. and then treated with TFAA (2.65 ml, 18.73 mmol) at 0° C. Then the mixture was allowed to warm up to 25° C. and stirred for 18 h. The reaction mixture was washed with water and aqueous NaHCO$_3$, then dried over Na$_2$SO$_4$, filtered and concentrated. The mixture was purified by column chromatography (PE:EtOAc=8/1) to give 1-12.

$^1$H NMR (CDCl$_3$, 400 MHz) δ 7.00-7.34 (m, 5H), 4.50-4.63 (m, 3H), 4.16 (brs, 1H), 3.40-3.68 (m, 2H), 2.25-2.49 (m, 1H), 1.96-2.20 (m, 1H), 1.49 (s, 9H).

Preparation of (2S,4S)-Tert-Butyl 4-(Benzyloxy)-2-Cyano-2-(Cyclobutylmethyl)Pyrrolidine-1-Carboxylate (1-13)

To a mixture of 1-12 (1 g, 3.31 mmol) in THF (40 mL) at −78° C. under N$_2$ was added LDA (6.61 ml, 6.61 mmol) and HMPA (0.575 ml, 3.31 mmol) dropwise. The reaction mixture was stirred at this temperature for 1 h. And then (bromomethyl)cyclobutane (0.739 g, 4.96 mmol) was added dropwise at −78° C. and stirred at this temperature for 1 h. The reaction was quenched with NH$_4$Cl (aq), extracted with EtOAc (50 mL×3). The combined organic layers were washed with brine (50 mL), dried over Na$_2$SO$_4$, filtered and the filtrate was concentrated in vacuum to give crude product. The crude product was purified by chromatography (PE:EtOAc=10:1) to give 1-13.

$^1$H NMR (CDCl$_3$, 400 MHz) δ 7.27-7.17 (m, 5H), 4.43-4.49 (m, 3H), 3.95 (s, 1H), 3.27-3.30 (m, 1H), 2.50-2.54 (m, 1H), 2.25-2.33 (m, 2H), 1.36-2.20 (m, 8H), 1.59 (s, 9H).

Preparation of (2S,4S)-Tert-Butyl 2-(Aminomethyl)-2-(Cyclobutylmethyl)-4 Hydroxy Pyrrolidine-1-Carboxylate (1-14)

To a solution of 1-13 (130 mg, 0.351 mmol) in EtOH (10 mL) was added Raney nickel (206 mg, 3.51 mmol). Then the mixture was stirred at 25° C. for 8 hours under H$_2$. The reaction mixture was filtered and concentrated to give a crude product used in the next step without further purification. To a solution of above product (120 mg, 0.320 mmol) in HOAc (5 mL) was added Pd/C (5 mg, 0.047 mmol) at 25°

C., then the mixture was stirred at this temperature under H₂ for 18 h. The mixture was filtered and the filtrate was concentrated to give 1-14. It was used in the next step without purification.

Preparation of 5-Chloro-4-((((2S,4S)-2-(Cyclobutyl-methyl)-4-Hydroxypyrrolidinyl)Methyl)Amino)-2-Fluoro-N-(Thiazol-2-Yl)Benzenesulfonamide (1-15)

A mixture of 1-14 (81 mg, 0.176 mmol), 1-8 (50 mg, 0.176 mmol) and triethylamine (0.074 ml, 0.527 mmol) in DMF (5 mL) was stirred for 8 h at 25° C. under N₂. The mixture was concentrated by vacuo to give the crude product. The residue was purified by column chromatography (PE:EtOAc=1:1) to give a crude product. A mixture of the above product (50 mg, 0.069 mmol) and TFA (1 mL) in DCM (5 mL) was stirred at 25° C. for 2 h. After the reaction was complete, the mixture was concentrated by vacuo to give the crude product, which was purified by prep-HPLC to give 1-15.

¹H NMR (CD₃OD, 400 MHz) δ 7.74 (d, J=6.4 Hz, 1H), 7.11 (d, J=4.4 Hz, 1H), 6.73 (d, J=4.0 Hz, 1H), 6.63 (d, J=12.4 Hz, 1H), 4.56 (brs, 1H), 3.52-3.57 (m, 2H), 3.41-3.49 (m, 1H), 3.37-3.39 (m, 1H), 2.44-2.48 (m, 1H), 1.80-2.21 (m, 10H). LRMS m/z (M+H) 475.0. found, 475.1 required.

Example 1C 4-((((2S,4S)-2-(4-Bromobenzyl)-4-Hydroxypyrrolidin-2-Yl)Methyl)Amino)-5-Chloro-2-Fluoro-N-(Thiazol-2-Yl)Benzenesulfonamide (1-22, Method C)

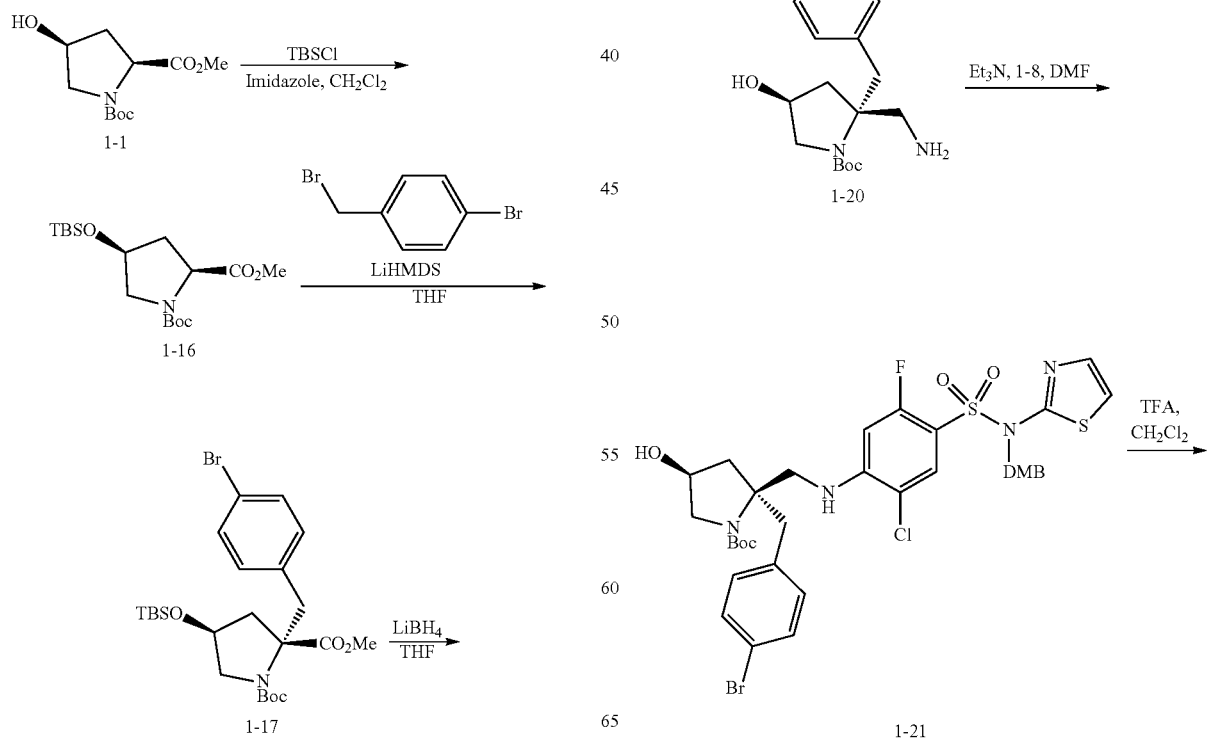

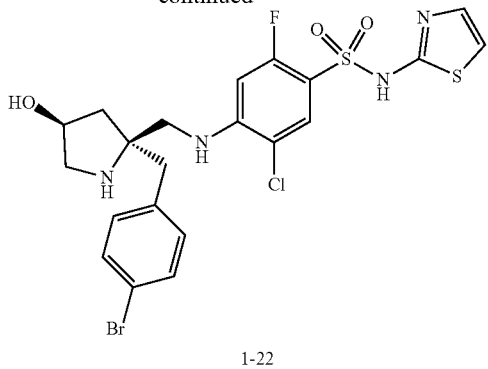

1-22

Preparation of (2S,4S)-1-Tert-Butyl 2-Methyl 4-((Tert-Butyldimethylsilyl)Oxy)Pyrrolidine-1,2-Dicarboxylate (1-16)

To a mixture of 1-1 (34 g, 139 mmol) and imidazole (28.3 g, 416 mmol) in DCM (250 ml) at 0° C. was added TBSCl (21.94 g, 146 mmol) in several portions, the resultant mixture was stirred at 15° C. for 15 hours. Then the reaction mixture was filtered and the filtrate was purified by column chromatography (PE:EtOAc=50:1-5:1) on silica gel to give 1-16.

$^1$H NMR (400 MHz, CDCl$_3$) δ 4.24-4.43 (m, 2H), 3.69 (s, 3H), 3.52-3.66 (m, 1H), 3.23-3.37 (m, 1H), 2.19-2.36 (m, 1H), 2.08 (dd, J=3.2, 12.8 Hz, 1H), 1.37-1.50 (m, 9H), 0.84 (d, J=4.0 Hz, 9H), 0.02 (d, J=3.6 Hz, 6H).

Preparation of (2S,4S)-1-Tert-Butyl 2-Methyl 2-(4-Bromobenzyl)-4-((Tert-Butyldimethylsilyl)Oxy) Pyrrolidine-1,2-Dicarboxylate (1-17)

To a mixture of LiHMDS (11.13 ml, 11.13 mmol) was added 1-16 (2 g, 5.56 mmol) in THF (30 mL) at −78° C. under N$_2$. The mixture was stirred at −78° C. for 1 h. 1-bromo-4-(bromomethyl)benzene (2.085 g, 8.34 mmol) was added dropwise into the mixture at −78° C.

The mixture was stirred at 25° C. for 4 h then quenched by NH$_4$Cl, extracted with EtOAc and washed with brine. The organic layers were dried over Na$_2$SO$_4$, filtered and the filtrate was concentrated in vacuo. The residue was purified by column chromatography on silica gel (PE:EtOAc=20:1) to give 1-17.

$^1$H NMR (400 MHz, CDCl$_3$) δ 7.55-7.64 (m, 2H), 7.12-7.25 (m, 2H), 3.92 (d, J=4.8 Hz, 3H), 3.38-3.72 (m, 2H), 3.10-3.32 (m, 3H), 2.11-2.32 (m, 2H), 1.55-1.70 (m, 9H), 0.87-1.01 (m, 9H), 0.17 (d, J=6.0 Hz, 1H), 0.02 (d, J=9.6 Hz, 5H)

Preparation of (2S,4S)-Tert-Butyl 2-(4-Bromobenzyl)-4-((Tert-Butyldimethylsilyl)Oxy)-2-(Hydroxymethyl)Pyrrolidine-1-Carboxylate (1-18)

To a solution of 1-17 (2.6 g, 4.92 mmol) in THF (50 mL) at 0° C. was added LiBH$_4$ (0.321 g, 14.76 mmol). The mixture was stirred at 25° C. for 20 h under N$_2$. Then the mixture was quenched with water and extracted with EtOAc. The combined organic phases were dried with Na$_2$SO$_4$, filtered and the filtrate was concentrated. The residue was purified by column chromatography on silica gel (PE:EtOAc=8:1) to give 1-18.

$^1$H NMR (400 MHz, CDCl$_3$) δ 7.39-7.49 (m, 2H), 6.98-7.16 (m, 2H), 3.72-3.99 (m, 2H), 3.33-3.63 (m, 3H), 3.03-3.23 (m, 2H), 2.76 (d, J=13.6 Hz, 1H), 2.05-2.14 (m, 1H), 1.51-1.64 (m, 9H), 0.82-1.01 (m, 9H), 0.05-0.20 (m, 6H)

Preparation of (2S,4S)-Tert-Butyl 2-(4-Bromobenzyl)-4-((Tert-Butyldimethylsilyl)Oxy)-2-((1,3-Dioxoisoindolin-2-Yl)Methyl)Pyrrolidine-1-Carboxylate (1-19)

To a mixture of 1-18 (2.2 g, 4.40 mmol), phthalimide (1.293 g, 8.79 mmol) and Ph$_3$P (2.306 g, 8.79 mmol) in THF (80 mL) was added DEAD (1.392 ml, 8.79 mmol) at 0° C. The mixture was stirred at 25° C. under N$_2$ for 36 h. Then the mixture was concentrated and the residue was purified by column chromatography on silica gel (PE:EtOAc=20:1) to give 1-19.

Preparation of (2S,4S)-Tert-Butyl 2-(Aminomethyl)-2-(4-Bromobenzyl)-4-Hydroxypyrrolidine-1-Carboxylate (1-20)

A solution of 1-19 (1.3 g, 2.065 mmol) and hydrazine (0.331 g, 10.32 mmol) in EtOH (40 mL) was stirred at 80° C. for 1 h. The mixture was filtered and the filtrate was concentrated in vacuum. The residue was purified by column chromatography on silica gel (EtOAc), and the product (100 mg) was mixed with TBAF (105 mg, 0.400 mmol) in THF (20 mL) and stirred at 25° C. for 3 hours. After three hours the mixture was concentrated in vacuo to give crude 1-20, which was used in the next step without further purification.

Preparation of (2S,4S)-Tert-Butyl 2-(4-Bromobenzyl)-2-(((2-Chloro-4-(N-(2,4-Dimethoxybenzyl)-N-(Thiazol-2-Yl)Sulfamoyl)-5-Fluorophenyl)Amino) Methyl)-4-Hydroxypyrrolidine-1-Carboxylate (1-21)

A mixture of 1-20 (115 mg, 0.249 mmol), 1-8 (80 mg, 0.208 mmol) and triethylamine (0.289 ml, 2.076 mmol) in 10 ml DMF was stirred at 50° C. under N$_2$ for 16 h. After the reaction was complete, the mixture was diluted with water, extracted with EtOAc. The organic layer was washed with water, brine, dried over Na$_2$SO$_4$, filtered and the filtrate was concentrated. The residue was purified by column chromatography on silica gel (PE:EtOAc=1:1) to give 1-21.

$^1$H NMR (400 MHz, CDCl$_3$) δ 7.71 (d, J=7.2 Hz, 1H), 7.32-7.47 (m, 3H), 7.20 (d, J 8.4 Hz, 1H), 7.11 (d, J=7.6 Hz, 2H), 6.95 (d, J=3.6 Hz, 1H), 633-6.38 (m, 2H), 6.26 (d, J 12.4 Hz, 1H), 5.18 (s, 2H), 3.75 (br. s., 8H), 3.56-3.64 (m, 1H), 3.47 (d, J=13.6 Hz, 1H), 3.06-3.29 (m, 3H), 2.12 (d, J=9.2 Hz, 1H), 1.82-1.93 (m, 1H), 1.49 (s, 9H) LRMS m/z (M+H) 825.1. found, 825.1 required.

Preparation of 4-((((2S,4S)-2-(4-Bromobenzyl)-4-Hydroxypyrrolidin-2-Yl)Methyl)Amino)-5-Chloro-2-Fluoro-N-(Thiazol-2-Yl)Benzenesulfonamide (1-22)

A mixture of 1-21 (20 mg, 0.024 mmol)) and TFA (1 ml, 12.98 mmol) in DCM (5 mL) was stirred at 25° C. for 1 h. Then the mixture was concentrated and the residue was purified by prep-HPLC to give 1-22.

$^1$H NMR (400 MHz, CD$_3$OD) δ 7.74 (d, J=7.2 Hz, 1H), 7.52 (d, J=8.4 Hz, 2H), 7.29 (d, J=8.4 Hz, 2H), 7.12 (d, J=4.4 Hz, 1H), 6.74 (d, J=4.4 Hz, 1H), 6.60 (d, J=12.4 Hz, 1H), 4.58 (br. s., 1H), 3.62-3.68 (m, 1H), 3.49-3.57 (m, 1H), 3.34-3.45 (m, 2H), 3.26 (d, J=13.4 Hz, 1H), 3.10-3.17 (m,

1H), 2.47-2.54 (m, 1H), 1.92 (d, J=14.4 Hz, 1H) LRMS m/z (M+H) 575.0 found, 575.0 required.

Example 1D 5-Chloro-2-Fluoro-4-((((2S,4S)-4-Hydroxy-2-Phenethylpyrrolidin-2-Yl)Methyl)-Amino)-N-(Thiazol-2-Yl)Benzenesulfonamide (1-28, Method D)

SCHEME 1D

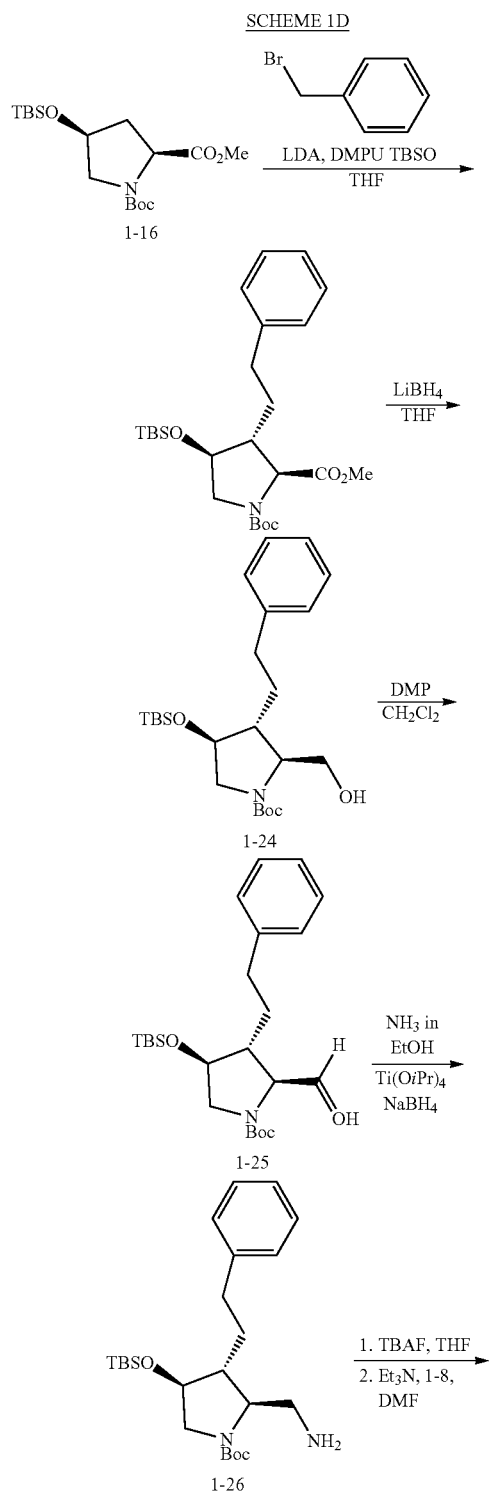

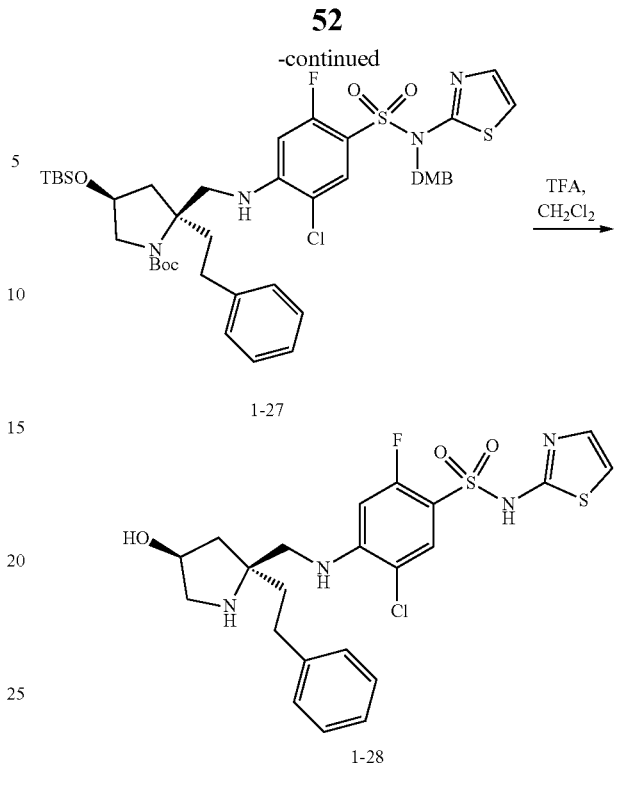

Preparation of (2S,4S)-1-Tert-Butyl 2-Methyl 4-((Tert-Butyldimethylsilyl)Oxy)-2-Phenethyl-Pyrrolidine-1,2-Dicarboxylate (1-23)

To a solution of 1-16 (500 mg, 1.39 mmol) in THF (3 mL) was added LDA (1.4 mL, 2.8 mmol) and DMPU (0.534 g, 4.17 mmol) at −78° C. The resulting solution was stirred at −78° C. for 40 min. Then (2-bromoethyl)benzene (0.386 g, 2.09 mmol) was added. The mixture was stirred at −78° C. for another 2 h and the reacting mixture was allowed to warm to 20° C. for 15 h. The reaction was quenched with NH$_4$Cl solution and extracted with EtOAc. The organic layer was washed with H$_2$O, brine and dried with anhydrous Na$_2$SO$_4$. After filtration, condensation and purified with prep-TLC (PE:EtOAc=10:1) to give 1-23.

$^1$H NMR (CDCl$_3$, 400 MHz) δ 7.18-7.28 (m, 2H), 7.04-7.16 (m, 3H), 4.30 (d, J=5.6 Hz, 1H), 3.66 (br. s., 3H), 3.30-3.50 (m, 1H), 3.27-3.37 (m, 1H), 2.44-2.57 (m, 2H), 2.32-2.42 (m, 1H), 2.25-2.32 (m, 1H), 2.17-2.23 (m, 1H), 2.05-2.16 (m, 1H), 1.34-1.48 (m, 9H), 0.73-0.91 (m, 9H), 0.01 (d, J=2.8 Hz, 6H)

Preparation of (2S,4S)-Tert-Butyl 4-((Tert-Butyldimethylsilyl)Oxy)-2-(Hydroxymethyl)-2-Phenethylpyrrolidine-1-Carboxylate (1-24)

To a solution of 1-23 (0.73 g, 1.57 mmol) in THF (10 mL) was added LiBH$_4$ (70 mg, 3.15 mmol). The mixture was stirred at 20° C. for 16 h. The reaction was quenched by MeOH dropwise until no bubbles appeared. The resulting mixture was concentrated under vacuum then purified by column chromatography (PE:EtOAc=50:1) to give 1-24.

$^1$H NMR (CDCl$_3$, 400 MHz) δ 7.18 (d, J=7.2 Hz, 5H), 5.00-5.28 (m, 1H), 4.09-4.30 (m, 1H), 3.60-3.78 (m, 1H), 3.44-3.58 (m, 2H), 3.13-3.30 (m, 1H), 2.60-2.83 (m, 1H), 2.25-2.49 (m, 2H), 2.09-2.23 (m, 1H), 1.90-2.05 (m, 1H), 1.58-1.73 (m, 1H), 1.37 (s, 9H), 0.82 (s, 9H), 0.01 (d, J=8.0 Hz, 6H)

Preparation of (2S,4S)-Tert-Butyl 4-((Tert-Butyldimethylsilyl)Oxy)-2-Formyl-2-Phenethylpyrrolidine-1-Carboxylate (1-25)

To a solution of 1-24 (480 mg, 1.1 mmol) in 10 mL DCM was added DMP (630 mg, 1.49 mmol), and the mixture was stirred at 20° C. for 0.5 h. TLC showed the reaction was complete. Then to the resulting solution was added saturated $Na_2S_2O_3$ and DCM. The organic layer was washed with saturated $NaHCO_3$, brine and dried with $Na_2SO_4$. Concentration and purification by column chromatography (PE: EtOAc=9:1), yielded 1-25.

$^1$H NMR (CDCl$_3$, 400 MHz) δ 9.34 (s, 1H), 7.18-7.26 (m, 2H), 7.13 (br. s., 3H), 4.20-4.396 (m, 1H), 3.61-3.92 (m, 1H), 3.10-3.33 (m, 1H), 2.63-2.83 (m, 1H), 2.45-2.60 (m, 1H), 2.03-2.39 (m, 3H), 1.78-1.99 (m, 1H), 1.28-1.42 (m, 9H), 0.79-0.90 (m, 9H), 0.00 (s, 6H)

Preparation of (2S,4S)-Tert-Butyl 2-(Aminomethyl)-4-((Tert-Butyldimethylsilyl)Oxy)-2 Phenethylpyrrolidine-1-Carboxylate (1-26)

To the solution of 1-25 (730 mg, 1.68 mmol) in 20 mL EtOH was bubbled with $NH_3$ at −78° C. Then Ti(iPrO)$_4$ (0.574 g, 2 mmol) was added. The solution was stirred at 20° C. for 24 h. To the resulting mixture was added NaBH$_4$ (32 mg, 0.84 mmol). The resulting mixture was stirred at 20° C. for 2 h. Purification by column chromatography (PE: EtOAc=5:1-1:0) to give 1-26.

$^1$H NMR (CDCl$_3$, 400 MHz) δ 7.15-7.21 (m, 2H), 6.98-7.13 (m, 3H), 5.19-5.24 (m, 1H), 4.14-4.31 (m, 1H), 3.45-3.65 (m, 1H), 3.25-3.43 (m, 1H), 2.99-3.24 (m, 1H), 2.58-2.77 (m, 1H), 2.28-2.49 (m, 2H), 2.12-2.25 (m, 1H), 1.99-2.11 (m, 1H), 1.83-1.98 (m, 1H), 1.58-1.80 (m, 1H), 1.40 (d, J=12.4 Hz, 9H), 0.81 (br. s., 9H), 0.17-0.15 (m, 6H).

Preparation of (2S,4S)-Tert-Butyl 2-(((2-Chloro-4-(N-(2,4-Dimethoxybenzyl)-N-(Thiazol-2-Yl)-Sulfamoyl)-5-Fluorophenyl)Amino)Methyl)-4-Hydroxy-2-Phenethylpyrrolidine-1Carboxylate (1-27)

To a solution of 1-26 (200 mg, 0.46 mmol) in 5 mL THF was added TBAF (156 mg, 0.6 mmol). The resulting mixture was stirred at 18° C. for 16 h. Purification by prep-TLC (DCM:MeOH:NH$_3$.H$_2$O=10:1:0.05) to give a product (120 mg, 81%). To a solution of above product (120 mg, 0.374 mmol) and 1-8 (173 mg, 0.374 mmol) in DMF (8 mL) was added triethylamine (190 mg, 1.87 mmol). The solution was stirred at 50° C. for 18 h. The resulting solution was concentrated and purified by prep-TLC (PE:EtOAc=1:1) to give 1-27.

Preparation of 5-Chloro-2-Fluoro-4-((((2S,4S)-4-Hydroxy-2-Phenethylpyrrolidin-2-Yl)Methyl)-Amino)-N-(Thiazol-2-Yl)Benzenesulfonamide (1-28)

The solution of 1-27 (230 mg, 0.3 mmol) in TFA (1.5 mL) and DCM (5 mL) was stirred at 16° C. for 1 h. After concentrated and purified by prep-HPLC, 1-28.

$^1$H NMR (CD$_3$OD, 400 MHz) δ7.75 (d, J=7.2 Hz, 1H), 7.20-7.30 (m, 4H), 7.14-7.19 (m, 1H), 7.12 (d, J=4.8 Hz, 1H), 6.66-6.80 (m, 2H), 4.62 (br. s., 1H), 3.69 (d, J=12.4 Hz, 2H), 3.34-3.51 (m, 2H), 2.65-2.88 (m, 2H), 2.40 (dd, J=4.4, 14.4 Hz, 1H), 1.98-2.25 (m, 3H). LRMS m/z (M+H) 511.0. found, 511.1 required.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 1

| Example (synthesis method) | Structure | Name | Data |
|---|---|---|---|
| 1-29 (method C) | 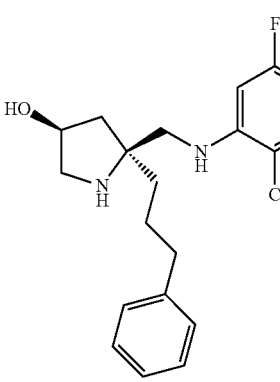 | 5-chloro-2-fluoro-4-(((((2S,4S)-4-hydroxy-2-(3-phenylpropyl)-pyrrolidin-2-yl)methyl)amino)-N-(thiazol-2-yl)-benzene-sulfonamide | $^1$HNMR (CD$_3$OD, 400 MHz) δ 7.72 (d, J = 7.2 Hz, 1H), 7.17-7.23 (m, 2H), 7.07-7.15 (m, 4H), 6.67-6.74 (m, 2H), 4.54 (br. s., 1H), 3.55-3.65 (m, 2H), 3.30-3.36 (m, 2H), 2.54-2.68 (m, 2H), 2.21 (dd, J = 4.4, 14.4 Hz, 1H), 2.03 (d, J = 14.4 Hz, 1H), 1.67-1.86 (m, 4H). LRMS m/z (M + H) 525.1 found, 525.5 required. |

TABLE 1-continued

| Example (synthesis method) | Structure | Name | Data |
|---|---|---|---|
| 1-30 (method C) | 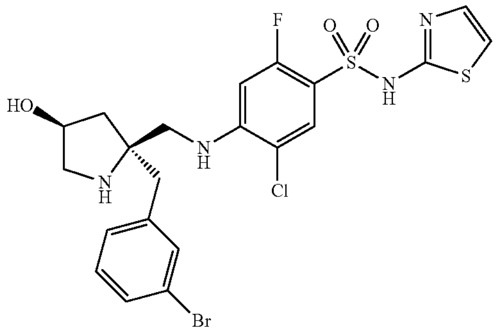 [SMILES: O=S(=O)(Nc1nccs1)c1cc(Cl)c(NC[C@]2(Cc3cccc(Br)c3)C[C@H](O)CN2)cc1F] | 4-((((2S,4S)-2-(3-bromobenzyl)-4-hydroxypyrrolidin-2-yl)methyl)amino)-5-chloro-2-fluoro-N-(thiazol-2-yl) benzenesulfonamide | $^1$H NMR (CD$_3$OD, 400 MHz) 7.76 (d, J = 5.4 Hz, 1H), 7.45-7.52 (m, 2H), 7.32-7.38 (m, 1H), 7.29 (d, J = 7.4 Hz, 1H), 7.12 (d, J = 4.8 Hz, 1H), 6.74 (d, J = 4.8 Hz, 1H), 6.58 (d, J = 12.4 Hz, 1H), 4.59 (s, 1H), 3.60-3.67(m, 1H), 3.50-3.57 (m, 1H), 3.41-3.47 (m, 1H), 3.34-3.38 (m, 1H), 3.26 (br. s., 1H), 3.11-3.17 (m, 1H), 2.52 (dd, J = 5.2, 14.4 Hz, 1H), 1.93 (d, J = 14.4 Hz, 1H). LRMS m/z (M + H) 575.0 found, 575.0 required. |
| 1-31 (method A) | 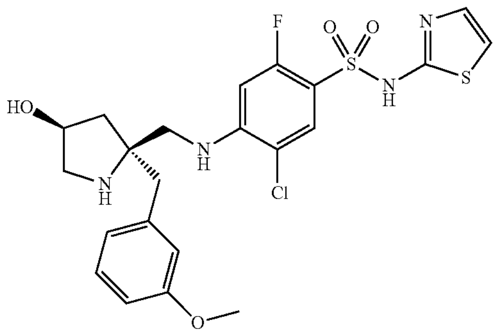 [SMILES: COc1cccc(C[C@@]2(CNc3cc(F)c(S(=O)(=O)Nc4nccs4)cc3Cl)C[C@H](O)CN2)c1] | 5-chloro-2-fluoro-4-((((2S,4S)-4-hydroxy-2-(3-methoxybenzyl) pyrrolidin-2-yl)methyl)amino)-N-(thiazol-2-yl) benzenesulfonamide | $^1$HNMR (CD$_3$OD, 400 MHz) 7.74 (d, J = 6.8 Hz, 1H), 7.25-7.29 (m, 1H), 7.10 (d, J = 4.8 Hz, 1H), 6.87-6.91 (m, 3H), 6.72 (d, J = 4.4 Hz, 1H), 6.55 (d, J = 12.8 Hz, 1H), 4.56 (brs, 1H), 3.72 (s, 3H), 3.55-3.65 (m, 2H), 3.30-3.35(m, 2H), 3.06-3.17 (m, 2H), 2.50-2.54 (m, 1H), 1.92-1.96 (m, 1H). LRMS m/z (M + H) 527.1 found, 527.1 required. |
| 1-32 (method A) | 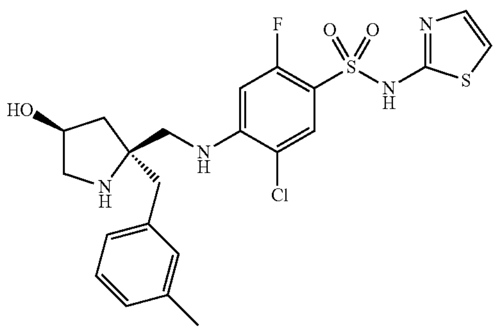 [SMILES: Cc1cccc(C[C@@]2(CNc3cc(F)c(S(=O)(=O)Nc4nccs4)cc3Cl)C[C@H](O)CN2)c1] | 5-chloro-2-fluoro-4-((((2S,4S)-4-hydroxy-2-(3-methoxybenzyl) pyrrolidin-2-yl)methyl)amino)-N-(thiazol-2-yl) benzenesulfonamide | $^1$H NMR (CD$_3$OD, 400 MHz) δ 7.74 (d, J = 7.2 Hz, 1H), 7.25 (t, J = 7.2 Hz, 1H), 7.17-7.03 (br. s., 4H), 6.72 (d, J = 4.8 Hz, 1H), 6.53 (d, J = 12.4 Hz, 1H), 4.55 (br. s., 1H), 3.69-3.49 (m, 2H), 3.42-3.32 (m, 2H), 3.24-3.02 (m, 2H), 2.52 (dd, J = 4.8, 14.4 Hz, 1H), 2.27 (s, 3H), 1.92 (d, J = 14.4 Hz, 1H) LRMS m/z (M + H) 511.0 found, 511.0 required. |
| 1-33 (method C) | 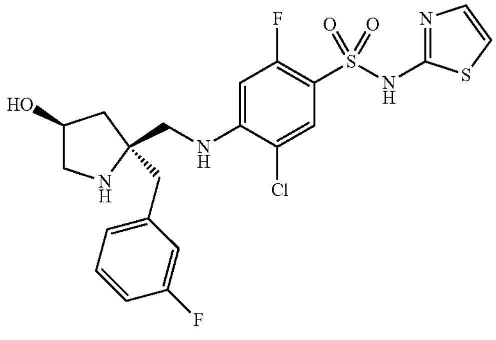 [SMILES: O=S(=O)(Nc1nccs1)c1cc(Cl)c(NC[C@]2(Cc3cccc(F)c3)C[C@H](O)CN2)cc1F] | 5-chloro-2-fluoro-4-((((2S,4S)-2-(3-fluorobenzyl)-4-hydroxypyrrolidin-2-yl)methyl)amino)-N-(thiazol-2-yl) benzenesulfonamide | $^1$HNMR (CD$_3$OD, 400 MHz) δ 7.72 (d, J = 6.0 Hz, 1H), 7.34 (d, J = 7.2 Hz, 1H), 7.15 (d, J = 7.4 Hz, 2H), 7.10 (d, J = 4.8 Hz, 1H), 7.05 (t, J = 8.4 Hz, 1H), 6.71 (d, J = 4.2 Hz, 1H), 6.41 (d, J = 11.6 Hz, 1H), 4.56 (br. s., 1H), 3.64 (d, J = 13.6 Hz, 1H), 3.53 (d, J = 13.6 Hz, 1H), 3.15-3.35 (m, 3H), 3.16 (d, J = 13.6 Hz, 1H), 2.24 (d, J = 14.1 Hz, 1H), 2.01 (dd, J = 4.9, 14.4 Hz, 1H). LRMS m/z (M + H) 515.0 found, 515.0 required. |

TABLE 1-continued

| Example (synthesis method) | Structure | Name | Data |
|---|---|---|---|
| 1-34 (method A) | 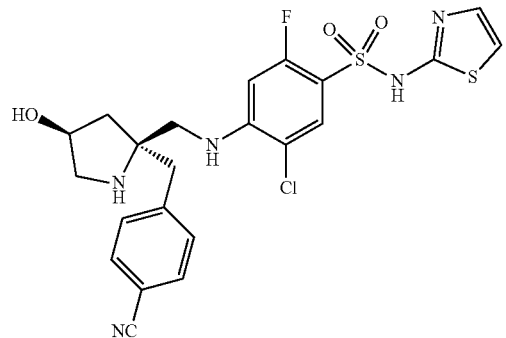 | 5-chloro-4-(((((2S,4S)-2-(3,3-dimethylbutyl)-4-hydroxypyrrolidin-2-yl)methyl)amino)-2-fluoro-N-(thiazol-2-yl)benzenesulfonamide | $^1$HNMR (CD$_3$OD, 400 MHz) δ 7.77(d, J = 6.8 Hz, 1H), 7.13 (d, J = 4.4 Hz, 1H), 6.80 (s, 1H), 6.76 (d, J = 4.8 Hz, 1H), 4.60 (s, 1H), 3.46-3.66 (m, 2H), 3.43 (d, J = 3.2 Hz, 1H), 3.33 (d, J = 2.0 Hz, 1H), 2.24 (d, J = 10.8 Hz, 1H), 2.17 (d, J = 11.2 Hz, 1H), 1.76~1.92 (m, 2H), 1.27-1.39 (m, 2H), 0.92 (s, 9H). LRMS m/z (M + H) 491.1 found, 491.1 required. |

Example 2 5-Chloro-4-(((((2S,4S)-2-(4-Cyanobenzyl)-4-Hydroxypyrrolidin-2-Yl)Methyl)Amino)-2-Fluoro-N-(Thiazol-2-Yl)Benzenesulfonamide (2-2) and 4-(((((2S,4S)-2-(4-(Aminomethyl) Benzyl)-4-Hydroxypyrrolidin-2-Yl) Methyl)Amino)-5-Chloro-2-Fluoro-N-(Thiazol-2-Yl)Benzenesulfonamide (2-3)

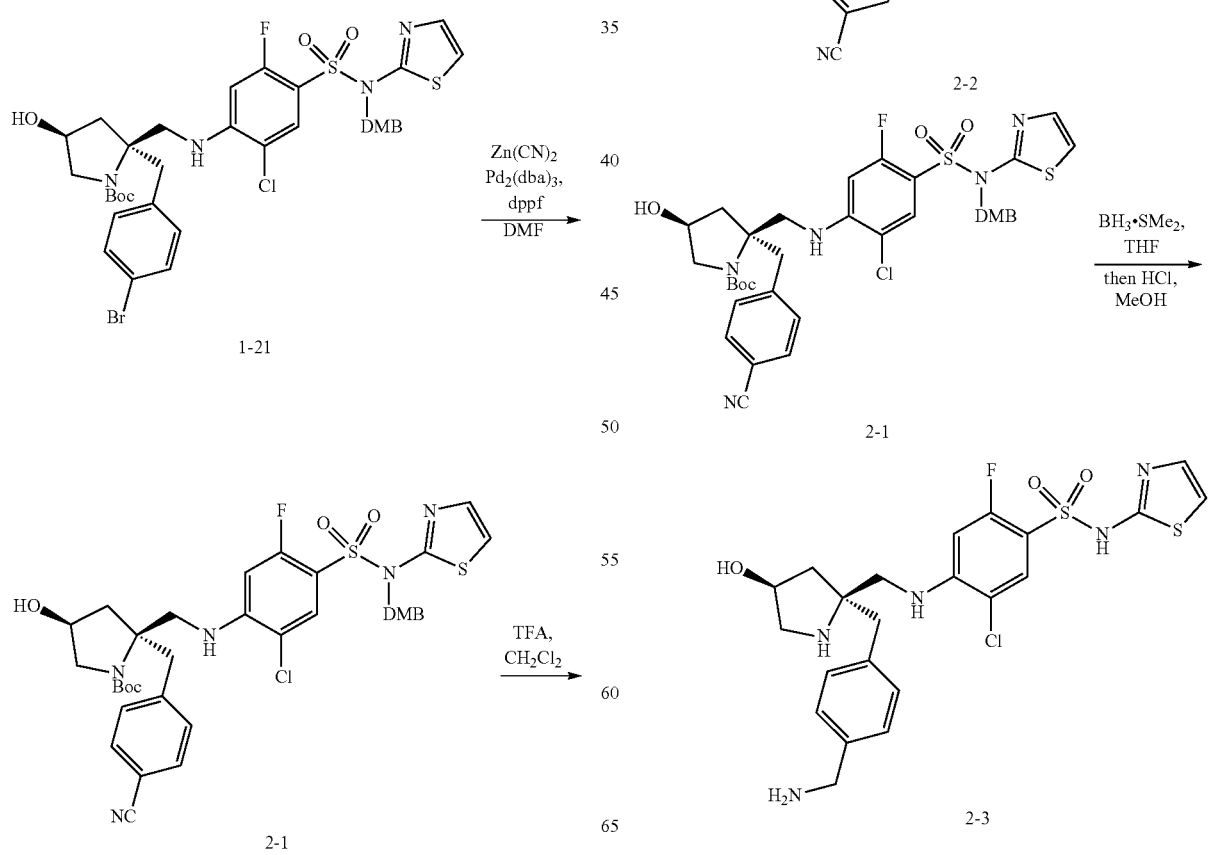

Preparation of (2S,4S)-Tert-Butyl 2-(((2-Chloro-4-(N-(2,4-Dimethoxybenzyl)-N-(Thiazol-2-Yl)Sulfamoyl)-5-Fluorophenyl)Amino)Methyl)-2-(4-Cyanobenzyl)-4-Hydroxypyrrolidine-1-Carboxylate (2-1)

To a mixture of 1-21 (100 mg, 0.121 mmol), dicyanozinc (9.95 mg, 0.085 mmol) and DPPF (13.42 mg, 0.024 mmol) in DMF (5 mL) was added Pd$_2$dba$_3$ (11.08 mg, 0.012 mmol). The mixture was stirred at 110° C. under N$_2$ for 12 h. Then the mixture was concentrated in vacuo and the residue was purified by prep-TLC (PE:EtOAc=1:1) to give 2-1.

Preparation of 5-Chloro-4-((((2S,4S)-2-(4-Cyanobenzyl)-4-Hydroxypyrrolidin-2-Yl)Methyl)Amino)-2-Fluoro-N-(Thiazol-2-Yl)Benzenesulfonamide (2-2)

To a solution of 2-1 (50 mg, 0.065 mmol) in DCM (5 ml) was added TFA (0.5 ml, 6.49 mmol). The mixture was stirred at 15° C. under N$_2$ for 1 h. Then the mixture was concentrated and the residue was purified by prep-HPLC to give 2-2.

$^1$H NMR (400 MHz, CD$_3$OD) δ 7.65-7.76 (m, 3H), 7.54 (d, J=7.6 Hz, 2H), 7.10 (d, J=4.8 Hz, 1H), 6.72 (d, J=4.8 Hz, 1H), 6.58 (d, J=12.4 Hz, 1H), 4.58 (br. s., 1H), 3.66 (d, J=14.0 Hz, 1H), 3.33-3.52 (m, 4H), 3.21-3.27 (m, 1H), 2.51 (dd, J=4.8, 14.4 Hz, 1H), 1.92 (d, J=14.4 Hz, 1H). LRMS m/z (M+H) 522.0. found, 522.0 required.

Preparation of 4-((((2S,4S)-2-(4-(Aminomethyl)Benzyl)-4-Hydroxypyrrolidin-2-Yl)Methyl)Amino)-5-Chloro-2-Fluoro-N-(Thiazol-2-Yl)Benzenesulfonamide (2-3)

To a mixture of 2-1 (50 mg, 0.065 mmol) in THF (10 mL) was added BH$_3$.DMS (0.123 ml, 1.295 mmol) at 0° C. The mixture was stirred at 15° C. for 18 h. Then MeOH (1 mL) was added into the mixture to quench the reaction and concentrated. Then the residue was stirred in HCl/MeOH (0.1 mL, 4M) and MeOH (10 mL) at 15° C. for 1 h. The resulting mixture was concentrated in vacuo. The residue was purified by prep-HPLC to give 2-3.

$^1$H NMR (400 MHz, CD$_3$OD) δ 7.72 (d, J=7.2 Hz, 1H), 7.46-7.42 (m, 4H), 7.10 (d, J 4.8 Hz, 1H), 6.72 (d, J=4.8 Hz, 1H), 6.52 (d, J=12.4 Hz, 1H), 4.57 (br. s., 1H), 4.09 (s, 2H), 3.60-3.66 (m, 1H), 3.41-3.52 (m, 2H), 3.35 (d, J=11.2 Hz, 2H), 3.16-3.23 (m, 1H), 2.50-2.59 (m, 1H), 1.88 (d, J=14.0 Hz, 1H). LRMS m/z (M+H) 526.1. found, 526.5 required.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 2

| Example | Structure | Name | Data |
| --- | --- | --- | --- |
| 2-4 | 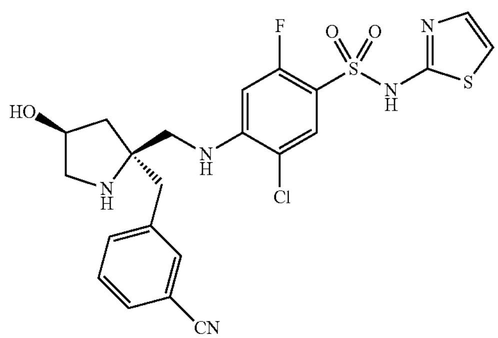 [SMILES: N#Cc1cccc(C[C@@]2(CNc3cc(F)c(S(=O)(=O)Nc4nccs4)cc3Cl)C[C@H](O)CN2)c1] | 5-chloro-4-((((2S,4S)-2-(3-cyanobenzyl)-4-hydroxypyrrolidin-2-yl)methyl)amino)-2-fluoro-N-(thiazol-2-yl)benzenesulfonamide | $^1$HNMR (CD$_3$OD, 400 MHz) δ 7.68-7.77 (m, 4H), 7.51-7.55 (m, 1H), 7.10 (d, J = 4.4 Hz, 1H), 6.72 (d, J = 4.4 Hz, 1H), 6.62 (d, J = 12.4 Hz, 1H), 4.58 (brs, 1H), 3.70-3.63 (m, 1H), 3.48-3.52 (m, 1H), 3.37-3.42 (m, 1H), 3.32-3.36 (m, 2H), 3.19-3.23 (m, 1H), 2.48-2.53 (m, 1H), 1.90-1.94 (m, 1H). LRMS m/z (M + H) 522.0 found, 522.0 required. |
| 2-5 | 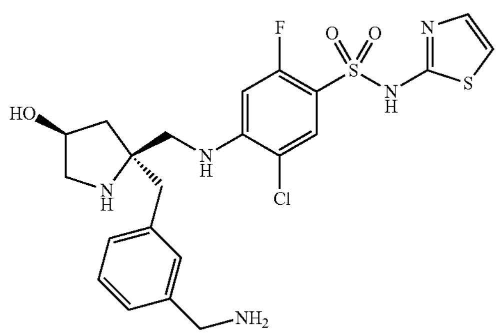 [SMILES: NCc1cccc(C[C@@]2(CNc3cc(F)c(S(=O)(=O)Nc4nccs4)cc3Cl)C[C@H](O)CN2)c1] | 4-((((2S,4S)-2-(3-(aminomethyl)benzyl)-4-hydroxypyrrolidin-2-yl)methyl)amino)-5-chloro-2-fluoro-N-(thiazol-2-yl)benzenesulfonamide | L-005406130: $^1$HNMR (CD$_3$OD, 400 MHz) δ 7.74 (d, J = 6.8 Hz, 1H), 7.43 (d, J = 10.0 Hz, 4H), 7.11 (d, J = 4.8 Hz, 1H), 6.73(d, J = 4.4 Hz, 1H), 6.58 (d, J = 4.4 Hz, 1H), 4.59 (s, 1H), 4.19 (s, 2H), 3.67 (d, J = 14.0 Hz, 1H), 3.54 (d, J = 14.0 Hz, 1H), 3.44-3.35 (m, 3H), 3.20 (d, J = 5.6 Hz, 1H), 2.54-2.58 (m, 1H), 1.92 (d, J = 14.0 Hz, 1H). LRMS m/z (M + H) 526.1 found, 526.1 required. |

Example 3 5-Chloro-2-Fluoro-4-((((2S,4S)-4-Hydroxy-2-(4-(Pyridin-2-Yl)Benzyl)Pyrrolidin-2-Yl)Methyl)Amino)-N-(Thiazol-2-Yl)Benzenesulfonamide (3-2)

SCHEME 3

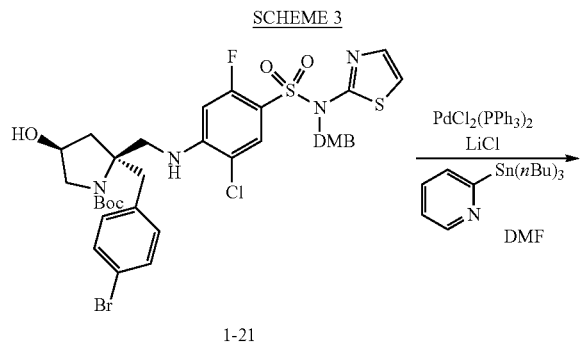

1-21

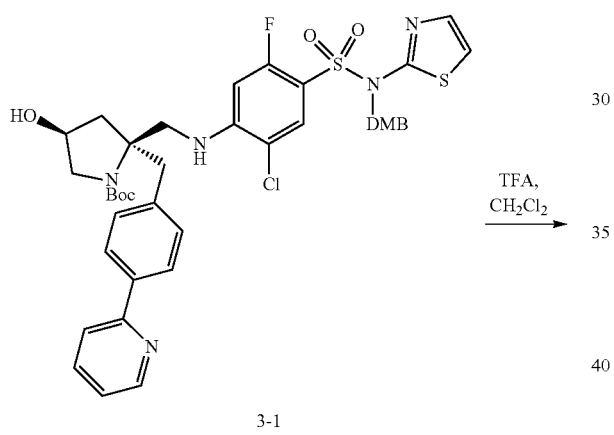

3-1

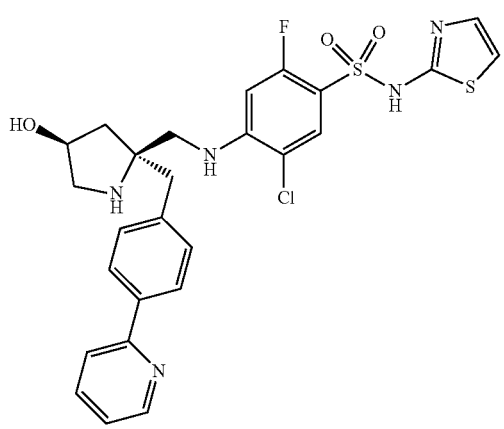

3-2

Preparation of (2S,4S)-Tert-Butyl 2-(((2-Chloro-4-(N-(2,4-Dimethoxybenzyl)-N-(Thiazol-2-Yl)Sulfamoyl)-5-Fluorophenyl)Amino)Methyl)-4-Hydroxy-2-(4-(Pyridin-2-Yl)Benzyl)Pyrrolidine-1-Carboxylate (3-1)

To a solution of 1-21 (100 mg, 0.121 mmol), 2-(tributylstannyl)pyridine (66.8 mg, 0.182 mmol) and lithium chloride (10.26 mg, 0.242 mmol) in DMF (5 ml) was added $PdCl_2(PPh_3)_2$ (8.50 mg, 0.012 mmol). The mixture was stirred at 100° C. under $N_2$ for 3 h. Then the mixture was quenched with water and extracted with EtOAc. The combined organic phases were dried with $Na_2SO_4$, filtered and the filtrate was concentrated. The residue was purified by prep-TLC (PE:EtOAc=1:1) to give 3-1.

Preparation of 5-Chloro-2-Fluoro-4-((((2S,4S)-4-Hydroxy-2-(4-(Pyridin-2-Yl)Benzyl)Pyrrolidin-2-Yl)Methyl)Amino)-N-(Thiazol-2-Yl)Benzenesulfonamide (3-2)

A mixture of 3-1 (40 mg, 0.049 mmol) and TFA (1 mL) in DCM (5 mL) was stirred at 20° C. for 2 h. After the reaction was complete, the mixture was concentrated by vacuo to give the crude product, which was purified by prep-HPLC to give 3-2.

$^1$H NMR (400 MHz, $CD_3OD$) δ 8.76 (brs, 1H), 8.36 (brs, 1H), 8.17 (brs, 1H), 7.95 (d, J 8.0 Hz, 1H), 7.61-7.74 (m, 5H), 7.11 (d, J=4.8 Hz, 1H), 6.73 (d, J=4.4 Hz, 1H), 6.58 (d, J 12.8 Hz, 1H), 4.62 (br. s., 1H), 3.70 (d, J=14.0 Hz, 1H), 3.58 (d, J=14.0 Hz, 1H), 3.48-3.51 (m, 3H), 3.31-3.38 (m, 1H), 2.58-2.63 (m, 1H), 1.97-2.03 (m, 1H).

LRMS m/z (M+H) 574.0. found, 574.1 required.

The following compounds were prepared using the methodology herein, but substituting the appropriately substituted reagent, as described in the Reaction Schemes and Examples. The requisite starting materials were commercially available, described in the literature or readily synthesized by one skilled in the art of organic synthesis without undue experimentation.

TABLE 3

| Example | Structure | Name | Data |
|---|---|---|---|
| 3-3 | 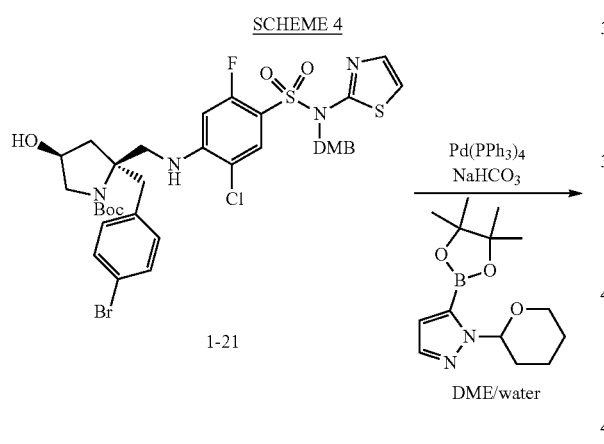 | 5-chloro-2-fluoro-4-((((2S,4S)-4-hydroxy-2-(4-(oxazol-2-yl)benzyl)pyrrolidin-2-yl)methyl)amino)-N-(thiazol-2-yl)benzenesulfonamide | $^1$H NMR (400 MHz, CD$_3$OD) δ 7.98-8.02 (m, 3H), 7.73 (d, J = 7.2 Hz, 1H), 7.51 (d, J = 8.4 Hz, 2H), 7.30 (s, 1H), 7.09 (d, J = 4.8 Hz, 1H), 6.72 (d, J = 4.4 Hz, 1H), 6.60 (d, J = 12.8 Hz, 1H), 4.58 (br. s., 1H), 3.71 (d, J = 14.0 Hz, 1H), 3.57 (d, J = 14.0 Hz, 1H), 3.30-3.40 (m, 3H), 3.20-3.28(m, 1H), 2.52-2.57 (m, 1H), 1.93-1.97 (m, 1H). LRMS m/z (M + H) 564.0 found, 564.1 required. |

Example 4 4-(((((2S,4S)-2-(4-(1H-Pyrazol-5-Yl)Benzyl)-4-Hydroxypyrrolidin-2-Yl) Methyl)Amino)-5-Chloro-2-Fluoro-N-(Thiazol-2-Yl)Benzenesulfonamide (4-2)

SCHEME 4

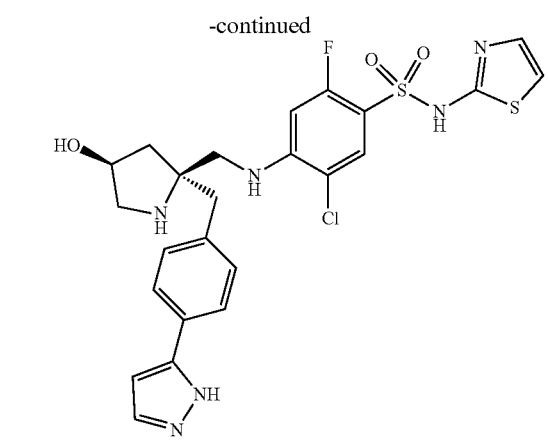

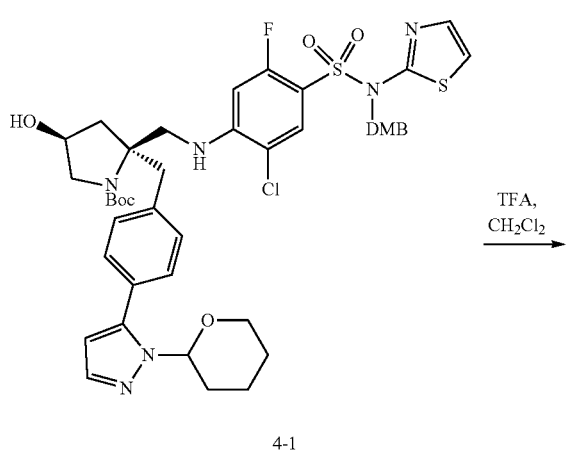

Preparation of (2S,4S)-Tert-Butyl 2-(((2-Chloro-4-(N-(2,4-Dimethoxybenzyl)-N-(Thiazol-2-Yl)Sulfamoyl)-5-Fluorophenyl)Amino)Methyl)-4-Hydroxy-2-(4-(1-(Tetrahydro-2H-Pyran-2-Yl)-1H-Pyrazol-5-Yl)Benzyl)Pyrrolidine-1-Carboxylate (4-1)

To a mixture of 1-21 (100 mg, 0.121 mmol) in DME (3 ml) under N$_2$ was added Pd(PPh$_3$)$_4$ (28.0 mg, 0.024 mmol), followed by the addition of 1-(tetrahydro-2H-pyran-2-yl)-5-(4,4,5,5-tetramethyl-1,3,2-dioxaborolan-2-yl)-1H-pyrazole (50.5 mg, 0.182 mmol) and NaHCO$_3$ (20.34 mg, 0.242 mmol) in Water (2 ml). The reaction mixture was refluxed at 90° C. for 16 h. The organic solvent was removed under reduced pressure. The crude residue was purified by prep-TLC (PE:EtOAc=1:2) to give 4-1.

Preparation of 4-(((((2S,4S)-2-(4-(1H-Pyrazol-5-Yl)Benzyl)-4-Hydroxypyrrolidin-2-Yl)Methyl)Amino)-5-Chloro-2-Fluoro-N-(Thiazol-2-Yl)Benzenesulfonamide (4-2)

To a solution of 4-1 (40 mg, 0.045 mmol) in DCM (5 ml) was added TFA (0.5 ml, 6.49 mmol). The mixture was stirred at 15° C. under N$_2$ for 1 h. Then the mixture was concentrated and the residue was purified by prep-HPLC to give 4-2.

¹H NMR (400 MHz, CD₃OD) δ 7.70-7.84 (m, 3H), 7.66 (d, J=1.6 Hz, 1H), 7.41 (d, J=7.6 Hz, 2H), 7.09 (d, J=4.8 Hz, 1H), 6.64-6.76 (m, 2H), 6.61 (d, J=12.4 Hz, 1H), 4.57 (br. s., 1H), 3.54-3.70 (m, 2H), 3.30-3.42 (m, 3H), 3.14-3.21 (m, 1H), 2.55 (dd, J=4.8, 14.4 Hz, 1H), 1.94 (d, J=14.4 Hz, 1H). LRMS m/z (M+H) 563.1. found, 563.1 required.

Core Synthesis Examples

Example I-1 5-Chloro-N-(2,4-Dimethoxybenzyl)-2,4-Difluoro-N-(Thiazol-2-Yl)Benzene Sulfonamide (6-5)

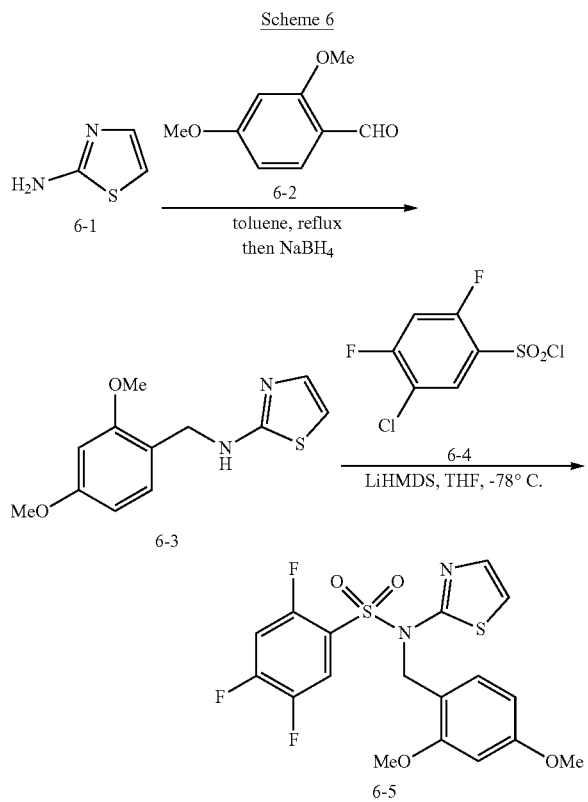

Preparation of N-(2,4-Dimethoxybenzyl)Thiazol-2-Amine (6-3)

A mixture of 6-1 (100 g, 1 mol) and 6-2 (151 g, 0.91 mol) in 2 L of toluene was refluxed for 8 h with Dean-Stark apparatus to remove water. The mixture was cooled and the solvent was evaporated in vacuo. To the residue was added 3 L of MeOH and the resulting mixture was cooled to 0° C. NaBH₄ (151 g, 4 mol) was added carefully in portions. The mixture was then warmed to room temperature and stirred for 4 h. The mixture was quenched with water, then MeOH was evaporated in vacuo. The water layer was extracted with EtOAc and the combined organic layers were dried over Na₂SO₄, filtered and concentrated. The residue was purified by column chromatography on silica gel (PE:EtOAc=5:1 to 2:1) to give the product of 6-3. ¹H NMR (400 MHz CD₃OD) δ 7.16 (d, J=8.4 Hz, 1H), 6.97 (d, J=4.0 Hz, 1H), 6.50-6.52 (m, 2H), 6.44 (dd, J=8.0, 2.0 Hz, 1H), 4.35 (s, 2H), 3.81 (s, 3H), 3.76 (s, 3H).

Preparation of 5-Chloro-N-(2,4-Dimethoxybenzyl)-2,4-Difluoro-N-(Thiazol-2-Yl)Benzene Sulfonamide (6-5)

Under an atmosphere of nitrogen, 6-3 (5 g, 20 mmol) was dissolved in THF (100 mL) and cooled to −78° C. LiHMDS (24 mL, 24 mmol) was added dropwise keeping the temperature below −60° C. After 30 minutes, the cooling bath was removed and the reaction was warmed to room temperature for a further 30 minutes then cooled back to −78° C. A solution of 6-4 (5.54 g, 22.4 mmol) in THF (10 mL) was added dropwise keeping the temperature below −60° C. and the reaction mixture was warmed to room temperature. Saturated aqueous ammonium chloride solution (50 mL) was added followed by water to dissolve the solid which had precipitated out. The aqueous layer was extracted with ethyl acetate (50 mL) and the organic extracts was dried over Na₂SO₄, filtered and concentrated. The residue was purified by column chromatography on silica gel (PE:EtOAc=10:1) to give the product of 6-5.

¹H NMR (400 MHz CDCl₃) δ 7.88~7.92 (m, 1H), 7.40 (d, J=4.0, 1H), 7.16~7.18 (m, 1H), 6.96~7.01 (m, 2H), 6.32~6.36 (m, 2H), 5.16 (s, 2H), 3.74 (s, 3H), 3.71 (s, 3H); MS (M+H)⁺: 461

The following cores were made by analogy to Example 6 using commercially available sulfonyl chlorides and amines:

Example I-2 5-Chloro-N-(5-Chlorothiazol-2-Yl)-N-(2,4-Dimethoxybenzyl)-2,4-Difluoro Benzenesulfonamide (7-1)

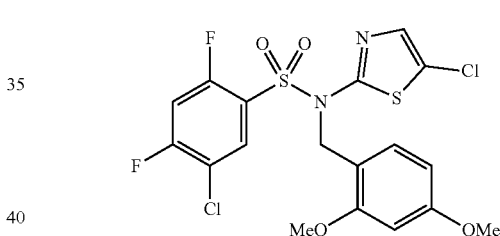

¹H NMR (400 MHz CDCl₃) δ 7.88 (t, J=7.2 Hz, 1H), 7.24 (s, 1H), 7.18 (d, J=8.0 Hz, 1H), 7.00 (t, J=8.8 Hz, 1H), 6.37 (dd, J=8.4, 2.4 Hz, 1H), 6.32 (d, J=2.4 Hz, 1H), 5.12 (s, 2H), 3.77 (s, 3H), 3.73 (s, 3H).

Example I-3 5-Chloro-N-(2,4-Dimethoxybenzyl)-2,4-Difluoro-N-(5-Fluorothiazole-2-Yl)Benzenesulfonamide (8-1)

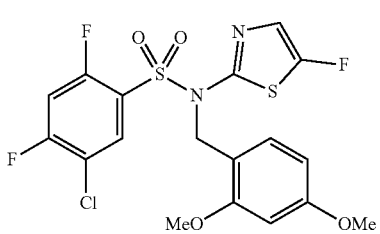

¹H NMR (400 MHz CDCl₃) δ 7.87 (t, J=7.6 Hz, 1H), 7.16 (d, J=8.4 Hz, 1H), 7.01~7.06 (m, 2H), 6.38 (dd, J=8.4, 2.4 Hz, 1H), 6.33 (d, J=2.4 Hz, 1H), 5.04 (s, 2H), 3.77 (s, 3H), 3.72 (s, 3H).

IonWorks® Experimental Procedure

Compounds were tested on human Nav1.7 and Nav1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Nav1.7 and 1.5 channels. Cells were sealed on a planar substrate using the Population Patch Plate (PPC) technology. Electrical access was obtained using both nystatin and amphotericin. A double-pulse protocol was used for the determination of $IC_{50}$ values for inactivated state block. Nav1.7 and Nav1.5 expressing cells were voltage clamped at −100 mV and −110 mV, respectively. A depolarizing prepulse to −10 mV (Nav1.7) or −30 mV (Nav1.5) for 1000 ms followed by a 10 ms repolarization to −100 mV (Nav1.7) or −110 mV (Nav1.5) was given to generate fractional channel inactivation of ∼ 50%, followed by a 10 ms test pulse to −10 mV (Nav1.7) or −30 mV (Nav1.5) to measure peak current in control conditions and after compound addition. The following recording solutions were used (mM). External: 150 NaCl, 2 $CaCl_2$), 5 KCl, 1 Mg $Cl_2$, 10 HEPES, 12 Dextrose; internal: 120 CsF, 30 CsCl, 10 EGTA, 5 HEPES, 5 NaF, 2 $MgCl_2$.

For all electrophysiology experiments, offline analysis was used to determine percent inhibition as a function of drug concentration. $IC_{50}$ values were determined by fitting to the Hill equation.

The various compounds in Examples 1 through 4 and Tables 1 through 3 exemplified above were assayed for activity and selectivity using the foregoing IonWorks® technique. The results are reported in the following paragraph in a format expressing the identification of the compound with reference Example and compound (e.g. Ex 1-9 is Example 1, compound 9) followed by the observed potency in nM and the ratio of $Na_v1.7$ potency:$Na_v$ 1.5 potency as described here. Thus, Ex1-9: 1.7=8/ratio=3976 identifies compound Example 1, compound 9 as having 8 nM potency for the Nav 1.7 sodium ion channel (as measured by IonWorks®) and a ratio of 3976 $Na_v$ 1.7:$Na_v$ 1.5 potency, determined by IonWorks® measurement. The following results are reported:

IonWorks® Data

Ex1-9: 1.7=8/ratio>3976; Ex1-15: 1.7=4/ratio>7500; Ex1-22: 1.7=4/ratio=84; Ex1-28: 1.7=3/ratio=11000; Ex1-29: 1.7=2/ratio=10500; Ex1-30: 1.7=7/ratio=1220; Ex1-31: 1.7=7/ratio=4714; Ex1-32: 1.7=2/ratio=16500; Ex1-33: 1.7=7/ratio=1714; Ex1-34: 1.7=4/ratio=6750; Ex2-2: 1.7=4/ratio=3000; Ex2-3: 1.7=38/ratio=868; Ex2-4: 1.7=11/ratio=2909; Ex2-5: 1.7=4/ratio=6250; Ex3-2: 1.7=7/ratio=543; Ex3-3: 1.7=9/ratio=933; Ex4-2: 1.7=18/ratio=367.

We claim:

1. A compound, or a pharmaceutically acceptable salt thereof, having the structure of Formula A:

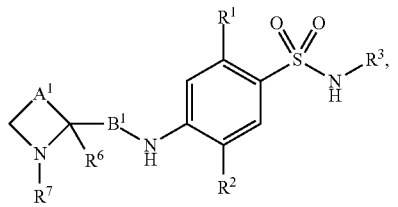

Formula A wherein:
$B^1$ is —$(CR^4R^5)_m$—,
  wherein:
    "m" is 1 or 2;
    $R^4$ and $R^5$ are independently for each occurrence: (i) —H; (ii) a cyclic-, branched-, or linear-alkenyl moiety of up to 6 carbon atoms; (iii) a cyclic-, branched- or linear-alkyl moiety of up to 6 carbon atoms, which alkyl moiety is optionally substituted by one or more substituents which are independently:
    (a) an aryl moiety of up to 10 carbon atoms which aromatic moiety is optionally substituted with up to 3 substituents which are independently for each occurrence: (1) cyclic-, branched-, or linear-alkyl moiety of up to 4 carbon atoms which is optionally substituted with —$N(R^{1a})_2$, wherein "$R^{1a}$" is independently for each occurrence: H; or linear-, branched, or cyclic-alkyl of up to 4 carbon atoms; (2) branched-, or linear-alkoxy moiety of up to 4 carbon atoms; (3) halogen; (4) —CN; or (v) —$N(R^{2a})_2$, wherein "$R^{2a}$" is independently for each occurrence: H; or linear-, branched, or cyclic-alkyl of up to 4 carbon atoms;
    (b) a heteroaryl moiety, with up to 5 carbon atoms and at least one ring atom which is N, O, or S, which heteroaryl moiety is optionally substituted with up to 3 substituents which are, independently: (1) cyclic-, branched-, or linear-alkyl moiety of up to 4 carbon atoms which is optionally substituted with —$N(R^{3a})_2$, wherein "$R^{3a}$" is independently for each occurrence: H; or linear-, branched, or cyclic-alkyl of up to 4 carbon atoms; (2) branched-, or linear-alkoxy moiety of up to 4 carbon atoms; (3) halogen; (4) —CN; or (v) —$N(R^{4a})_2$, wherein "$R^{4a}$" is independently for each occurrence: H; or linear-, branched, or cyclic-alkyl of up to 4 carbon atoms
    (c) halogen;
    (d) —CN; or
    (e) —$N(R^{5a})_2$, wherein "$R^{5a}$" is independently for each occurrence: (1) H; (2) linear-, branched, or cyclic-alkyl of up to 4 carbon atoms;
$A^1$ is —$(CR^{10}R^{11})_n$—, wherein:
  "n" is 1, 2, or 3;
  in at least one occurrence one of $R^{10}$ or $R^{11}$ is selected to be —OH; and
  the remaining occurrences of $R^{10}$ and $R^{11}$ are independently for each occurrence:
    (a) hydrogen;
    (b) halogen;
    (c) —OH;
    (d) —$N(R^{1e})_2$, wherein "$R^{1e}$" is, independently for each occurrence, (i) —H; or (ii) lower alkyl;
    (e) a branched-, cyclic- or linear-alkyl moiety of up to 6 carbon atoms which is optionally substituted with one or more substituents which are, independently for each occurrence:
      (i) halogen;
      (ii) —$N(R^{2e})_2$, wherein "$R^{2e}$" is, independently for each occurrence: (1) —H; or (2) lower alkyl;
      (iii) -OH;
      (iv) an aryl moiety which is optionally substituted with one or more, independently, cyclic-, branched-, or linear-alkoxy moiety of up to 4 carbon atoms; or (v) a heteroaryl moiety with up to 5 carbon atoms and at least one heteroatom, and which heteroaryl moiety may be optionally substituted with one or more cyclic-, branched-, or linear-alkoxy moiety with up to 6 carbon atoms;
(f) an aryl moiety which is optionally substituted with one or more substituents which are independently:
  (i) a cyclic-, branched-, or linear-alkyoxy moiety of up to 4 carbon atoms; or
  (ii) —OH; or
(g a heteroaryl moiety, with up to 5 carbon atoms and at least one heteroatom, wherein said heteroaryl moiety is optionally substituted with one or more substituents which are independently: (i) —CN; (ii) —OH; (iii) halogen, that is —F or —Br; (iv) cyclic-, branched-, or linear-alkyl of up to 6 carbon atoms, which alkyl moiety is optionally substituted with: —OH; —CN; halogen; or —N($R^{13e}$)$_2$, wherein "$R^{13e}$" is, independently for each occurrence: —H or lower alkyl; or (iv) cyclic-, branched-, or linear-alkoxy of up to 6 carbon atoms,
with the proviso that if "$R^{10}$" and "$R^{11}$" are selected to provide more than one occurrence of —OH, then the selection is made to preclude both germinal —OH and —OH depending from two adjacent carbon atoms;

$R^6$ is:
(c) a branched-, cyclic- or linear-alkyl of up to 6 carbon atoms which is substituted with one or more substituents which are, independently for each occurrence:
  (ii) N($R^{2b}$)$_2$, wherein "$R^{2b}$" is, independently for each occurrence, —H or lower alkyl;
  (v) an aryl moiety, with up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N($R^{3b}$)$_2$, wherein "$R^{3b}$" is, independently for each occurrence, —H or lower alkyl; (5) —N($R^{4b}$)$_2$, wherein "$R^{4b}$" is, independently for each occurrence, —H or lower alkyl; (6) cyclic-, branched-, or linear-alkoxy of up to 4 carbon atoms; (7) alkyl-thiol-moiety of up to 4 carbon atoms; (8) alkyl-sulfonyl moiety of up to 4 carbon atoms; or (9) a heterocycle moiety with up to 5 carbon atoms and one or more heteroatoms which are N, O, or S;
  (vi) a heteroaryl moiety with up to 4 carbon atoms and at least one heteroatom, wherein said heteroaryl moiety is optionally substituted with one or more substituents which are independently: (a) —CN; (b) —OH; (c) halogen; (d) cyclic-, branched-, or linear-alkyl of up to 4 carbon atoms, which alkyl moiety is optionally substituted with: —OH; —CN; halogen; or N($R^{5b}$)$_2$, wherein "$R^{5b}$" is, independently for each occurrence, —H or lower alkyl; or (e) cyclic-, branched-, or linear-alkoxy of up to 4 carbon atoms;
(d) an aryl moiety, with up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N($R^{1c}$)$_2$, wherein "$R^{1c}$" is, independently for each occurrence, —H or lower alkyl; (5) —N($R^{2c}$)$_2$, wherein "$R^{2c}$" is, independently for each occurrence, —H or lower alkyl; (6) cyclic-, branched-, or linear-alkoxy of up to 4 carbon atoms; (7) alkyl-thiol-moiety of up to 4 carbon atoms; (8) alkyl-sulfonyl moiety of up to 4 carbon atoms; or (9) a heterocycle moiety with up to 5 carbon atoms and one or more heteroatoms which are N, O, or S;
(e) a heteroaryl moiety with up to 4 carbon atoms and at least one heteroatom, wherein said heteroaryl moiety is optionally substituted with one or more substituents which are independently: (a) —CN; (b) —OH; (c) halogen; (d) cyclic-, branched-, or linear-alkyl of up to 4 carbon atoms, which alkyl moiety is optionally substituted with: —OH; —CN; halogen; or N($R^{3c}$)$_2$, wherein "$R^{3c}$" is, independently for each occurrence, —H or lower alkyl; or (e) cyclic-, branched-, or linear-alkoxy of up to 4 carbon atoms; or
(f) a heterocycle moiety, with up to 5 carbon atoms and one or more heteroatoms which are N, O, or S, $R^7$ is:
(a) —H;
(b) A cyclic-, branched-, or linear-alkyl moiety of up to 7 carbon atoms which is optionally substituted with one or more moieties which are, independently:
  (i) halogen;
  (ii) N($R^{1d}$)$_2$, wherein "$R^{1d}$" is, independently for each occurrence, —H or lower alkyl;
  (iii) lower alkyl;
  (iv) lower alkoxy;
  (v) an aryl moiety, with up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N($R^{2d}$)$_2$, wherein "$R^{2d}$" is, independently for each occurrence, —H or lower alkyl; (5) —N($R^{3d}$)$_2$, wherein "$R^{3d}$" is, independently for each occurrence, —H or lower alkyl; (6) cyclic-, branched-, or linear-alkoxy of up to 4 carbon atoms; (7) a heterocycle moiety, as defined herein, with comprising up to 5 carbon atoms and one or more heteroatoms which are N, O, or S; or
  (vi) a heteroaryl moiety, with up to 4 carbon atoms and at least one heteroatom, wherein said heteroaryl moiety is optionally substituted with one or more substituents which are independently: (a) —CN; (b) —OH; (c) halogen; (d) cyclic-, branched-, or linear-alkyl of up to 4 carbon atoms, which alkyl moiety is optionally substituted with: —OH; —CN; halogen; or N($R^{4d}$)$_2$, wherein "$R^{4d}$" is, independently for each occurrence, —H or lower alkyl; or (e) cyclic-, branched-, or linear-alkoxy of up to 4 carbon atoms; or
(vii) —OH, with the proviso that "—OH" is not selected as a substituent on a carbon atom bonded adjacent to the nitrogen atom;
(c) an aryl moiety, with up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or $N(R^{5d})_2$, wherein "$R^{5d}$" is, independently for each occurrence, —H or lower alkyl; (5) —$N(R^{6d})_2$, wherein "$R^{6d}$" is, independently for each occurrence, —H or lower alkyl; (6) cyclic-, branched-, or linear-alkoxy of up to 4 carbon atoms; (7) alkyl-thiol-moiety of up to 4 carbon atoms; (8) alkyl-sulfonyl moiety of up to 4 carbon atoms; or (9) a heterocycle moiety with up to 5 carbon atoms and one or more heteroatoms which are N, O, or S;
(d) a heteroaryl moiety, with up to 4 carbon atoms and at least one heteroatom, wherein said heteroaryl moiety is optionally substituted with one or more substituents which are independently: (a) —CN; (b) —OH; (c) halogen; (d) cyclic-, branched-, or linear-alkyl of up to 4 carbon atoms, which alkyl moiety is optionally substituted with: —OH; —CN; halogen; or $N(R^{7d})_2$, wherein "$R^{7d}$" is, independently for each occurrence, —H or lower alkyl; or (e) cyclic-, branched-, or linear-alkoxy of up to 4 carbon atoms; or
(e) a heterocycle moiety, with up to 5 carbon atoms and one or more heteroatoms which are N, O, or S;
$R^1$ and $R^2$ are independently for each occurrence: (a) hydrogen; (b) halogen; (c) —CN; or (d) $C_{1-6}$-alkyl, wherein one or more of the carbon atoms is partially or fully substituted with halogen or $C_{1-4}$-alkyl; and
$R^3$ is
(i) a moiety of Formula S1 or S2:

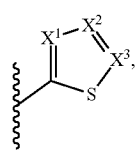

Formula S1

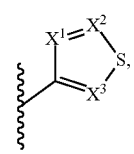

Formula S2 wherein one or two of $X^1$ to $X^3$ is —N= and the others are [=$CR^6$—], wherein "$R^6$" is:
(a) —H;
(b) an alkyl moiety which is —$C_{1-6}$-linear alkyl or —$C_{4-6}$-branched alkyl, which alkyl moiety is optionally substituted with one or more moieties which are independently for each occurrence: (a) halogen; or (b) —$C_{3-6}$-cycloalkyl, which is optionally substituted;
(c) $C_{1-6}$-linear alky-C(O)—O—, $C_{3-6}$-branched alkyl-C(O)—O— or $C_{3-6}$-cycloalkyl-C(O)—O—;
(d) —$C_{3-6}$-cycloalkyl optionally substituted with —F or $C_{1-6}$-linear alkyl; or
(e) halogen; or
(ii) a moiety of Formula S3:

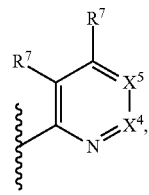

Formula S3 wherein:
"$X^4$" and "$X^5$" are independently [=N—] or [=$CR^7$—]; and
"$R^7$" is independently for each occurrence —H or —F, wherein no more than two "R" present in the moiety of S3 are selected to be "—F".

2. The compound of claim 1, or a pharmaceutically acceptable salt thereof, wherein "$B^1$" is —$CH_2$—.

3. The compound of claim 1 or a pharmaceutically acceptable salt thereof, wherein "$A^1$" is selected to be —$[CR^{10a}R^{11a}]_p$—, thereby providing a substituent of Formula $B^2$-a:

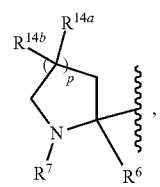

Formula $B^2$-a wherein:
"p" is 1 or 2;
one of "$R^{14a}$" or "$R^{14b}$" is selected to be —OH and the other occurrences of "$R^{14a}$" and "$R^{14b}$" are independently for each occurrence:
(a) —H;
(b) an aryl moiety which is optionally substituted on one or more ring carbon atoms with —OH or lower alkoxy;
(c) cyclic-, branched- or linear-alkyl moiety of up to 6 carbon atoms, which alkyl moiety is optionally substituted with one or more substituents which are, independently: (i) halogen; (ii) —OH; (iii) an aryl moiety which is optionally substituted with one or more substituents which are: (1) lower-alkoxy; (2) —$N(R^{1j})_2$, wherein "$R^{1j}$" is, independently for each occurrence —H or lower alkyl; or (3) —OH; (iv) a heteroaryl moiety with up to 5 ring carbon atoms and at least one nitrogen heteroatom, which moiety is optionally substituted on one or more ring carbon atoms with a substituent which is, independently, —OH or lower alkoxy; or (v) heterocycloalkyl with up to 6 carbon atoms and one or more heteroatoms selected from O, S, or N; or (d) —N(R$^{1j}$)$_2$, wherein "R$^{1j}$" is, independently for each occurrence: —H or lower alkyl; and "R$^6$" is:

(b) a branched-, cyclic- or linear-alkyl of up to 6 carbon atoms which is substituted with one or more substituents which are, independently for each occurrence:
  (ii) N(R$^{1k}$)$_2$, wherein "R$^{1k}$" is, independently for each occurrence, —H or lower alkyl;
  (iv) an aryl moiety with up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N(R$^{2k}$)$_2$, wherein "R$^{2k}$" is, independently for each occurrence, —H or lower alkyl; (5) —N(R$^{3k}$)$_2$, wherein "R$^{3k}$" is, independently for each occurrence, —H or lower alkyl;
  (v) a heteroaryl moiety with up to 4 carbon atoms and at least one heteroatom, wherein said heteroaryl moiety is optionally substituted with one or more substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N(R$^{4k}$)$_2$, wherein "R$^{4k}$" is, independently for each occurrence, —H or lower alkyl; (5) —N(R$^{5k}$)$_2$, wherein "R$^{5k}$" is, independently for each occurrence, —H or lower alkyl; or
  (vi) a heterocycloalkyl moiety with one or more heteroatoms which are N, O, or S;

(c) an aryl moiety, wherein the aryl ring of said moiety is optionally substituted with up to 3 substituents which are independently for each occurrence: (i) —CN; (ii) —OH; (iii) halogen; (iv) cyclic-, branched-, or linear-alkyl of up to 4 carbon atoms, which alkyl moiety is optionally substituted with: (1) —OH; (2) —CN; (3) halogen; or (4) —N(R$^{6k}$)$_2$, wherein "R$^{6k}$" is, independently for each occurrence, —H or lower alkyl; (v) —N(R$^{7k}$)$_2$, wherein "R$^{7k}$" is, independently for each occurrence, —H or lower alkyl; (vi) cyclic-, branched-, or linear-alkoxy of up to 4 carbon atoms;

(d) a heteroaryl moiety, wherein said heteroaryl has up to 5 ring carbon atoms and at least one heteroatom which is N, S, or O, and wherein said heteroaryl moiety is optionally substituted on one or more ring carbon atoms with a substituent which is independently for each occurrence: (i) —CN; (ii) —OH; (iii) halogen; (iv) cyclic-, branched-, or linear-alkyl of up to 4 carbon atoms, which alkyl moiety is optionally substituted with one or more substituents which are independently: (1) —OH; (2) —CN; (3) halogen; or (4) —N(R$^{8k}$)$_2$, wherein "R$^{8k}$" is, independently for each occurrence, —H or lower alkyl; or (v) cyclic-, branched-, or linear-alkoxy of up to 4 carbon atoms; or (e) a heterocycloalkyl moiety with up to 5 carbon atoms and one or more heteroatoms which are N, O, or S; and "R$^7$" is:

(a) —H;

(b) a cyclic-, branched-, or linear-alkyl moiety of up to 7 carbon atoms which is optionally substituted with one or more moieties which are, independently:
  (i) halogen, and when selected to be halogen is —F or —Cl;
  (ii) N(R$^{1L}$)$_2$, wherein "R$^{1L}$" is, independently for each occurrence: (1) —H; or (2) lower alkyl;
  (iii) lower alkyl;
  (iv) lower alkoxy;
  (v) an aryl moiety, with up to 6 ring carbon atoms, wherein the aryl ring of said moiety is optionally substituted with up to 3 substituents which are independently for each occurrence: (1) —CN; (2) —OH; (3) halogen, which is —F or —Br; (4) —N(R$^{3L}$)$_2$, wherein "R$^{3L}$" is, independently for each occurrence: (I) —H; or (II) lower alkyl; (5) cyclic-, branched-, or linear-alkyl of up to 4 carbon atoms, which alkyl moiety is optionally substituted with: (I) —OH; (II) —CN; (III) halogen; or (IV) —N(R$^{2L}$)$_2$, wherein "R$^{2L}$" is, independently for each occurrence: —H; or lower alkyl; (6) cyclic-, branched-, or linear-alkoxy of up to 4 carbon atoms; (7) a heterocycle moiety, with up to 5 carbon atoms and one or more heteroatoms which are N, O, or S;
  (vi) a heteroaryl moiety, with up to 4 carbon atoms and at least one heteroatom, said heteroaryl moiety is a 5-member heterocycle with at least one heteroatom which is N, S, or O, wherein said heteroaryl moiety is optionally substituted with one or more substituents which are independently: (1) —CN; (2) —OH; (3) halogen, which is: (I) —F; or (II) —Br; (4) cyclic-, branched-, or linear-alkyl of up to 4 carbon atoms, which alkyl moiety is optionally substituted with: (I) —OH; (II) —CN; (III) halogen; or (IV) N(R$^{4d}$)$_2$, wherein "R$^{4d}$" is, independently for each occurrence: —H; or lower alkyl; or (5) cyclic-, branched-, or linear-alkoxy of up to 4 carbon atoms; or
  (vii) -OH, with the proviso that "—OH" is not selected as a substituent on a carbon atom bonded adjacent to the nitrogen atom;

(c) an aryl moiety, with up to 6 ring carbon atoms, wherein the aryl ring of said moiety is optionally substituted with up to 3 substituents which are independently for each occurrence: (i) —CN; (ii) —OH; (iii) halogen, which is —F or —Br; (iv) cyclic-, branched-, or linear-alkyl of up to 4 carbon atoms, which alkyl moiety is optionally substituted with one or more substituents which are independently: (1) —OH; (2) —CN; (3) halogen; or (4) —N(R$^{5d}$)$_2$, wherein "R$^{5d}$" is, independently for each occurrence: (I) —H; or (II) lower alkyl; (5) —N(R$^{6d}$)$_2$, wherein "R$^{6d}$" is, independently for each occurrence: —H; or lower alkyl; (6) cyclic-, branched-, or linear-alkoxy of up to 4 carbon atoms; (7) alkyl-thiol-moiety of up to 4 carbon atoms, and when selected to be a thiol moiety is H$_3$C—S—; (8) alkyl-sulfonyl moiety of up to 4 carbon atoms, and when selected to be a sulfonyl moiety is H$_3$C—S(O)$_2$—; or (9) a heterocycle moiety, with up to 5 carbon atoms and one or more heteroatoms which are N, O, or S;

(d) a heteroaryl moiety, with up to 4 carbon atoms and at least one heteroatom, said heteroaryl moiety is a 5-member heterocycle with at least one heteroatom which is N, S, or O, wherein said heteroaryl moiety is optionally substituted with one or more substituents which are independently: (i) —CN; (ii) —OH; (iii) halogen, which is —F or —Br; (iv) cyclic-, branched-, or linear-alkyl of up to 4 carbon atoms, which alkyl moiety is optionally substituted with: (1) —OH; (2) —CN; (3) halogen; or (4) —N(R$^{7d}$)$_2$, wherein "R$^{7d}$" is, independently for each occurrence: (I) —H; or (II) lower alkyl; or (5) cyclic-, branched-, or linear-alkoxy of up to 4 carbon atoms; or (e) a heterocycle moiety, with up to 5 carbon atoms and one or more heteroatoms which are N, O, or S.

4. The compound of claim 3, or a pharmaceutically acceptable salt thereof, wherein, one occurrence of $R^{14a}$ or "$R^{14b}$" is —OH, and the other occurrences of "$R^{14a}$" and "$R^{14b}$" are independently for each occurrence: (a) —H; or (b) cyclic-, branched-, or linear-alkyl of up to 6 carbon atoms, which alkyl moiety is optionally substituted with one or more substituents which are, independently: (i) —OH; (ii) halogen; or (iii) —N($R^{1ba}$)$_2$, wherein "$R^{1ba}$" is, independently: (1) —H; or (2) lower-alkyl.

5. The compound of claim 1 or a pharmaceutically acceptable salt thereof, wherein "$A^1$" is selected to be —[HC(OH)—CR$^{10a}$R$^{11a}$]—, and "$R^7$" is "—H", thereby providing a substituent of Formula B²-b:

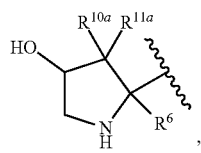

Formula B²-b wherein "$R^{10a}$" and "$R^{11a}$" are independently for each occurrence:
(a) —H;
(b) an aryl moiety which is optionally substituted on one or more ring carbon atoms with —OH or lower alkoxy;
(c) cyclic-, branched- or linear-alkyl moiety of up to 6 carbon atoms, which alkyl moiety is optionally substituted with one or more substituents which are, independently: (i) halogen; (ii) —OH; (iii) an aryl moiety which is optionally substituted with one or more substituents which are: (1) lower-alkoxy; (2) —N(R$^{1j}$)$_2$, wherein "R$^{1j}$" is, independently for each occurrence —H or lower alkyl; or (3) —OH; (iv) a heteroaryl moiety with up to 5 ring carbon atoms and at least one nitrogen heteroatom, which moiety is optionally substituted on one or more ring carbon atoms with a substituent which is, independently, —OH or lower alkoxy; or (v) heterocycloalkyl with up to 6 carbon atoms and one or more heteroatoms selected from O, S, or N; or
(d) —N(R$^{1j}$)$_2$, wherein "R$^{1j}$" is, independently for each occurrence: —H or lower alkyl; and "R$^6$" is:
(b) a branched-, cyclic- or linear-alkyl of up to 6 carbon atoms which is substituted with one or more substituents which are, independently for each occurrence:
(ii) N(R$^{1k}$)$_2$, wherein "R$^{1k}$" is, independently for each occurrence, —H or lower alkyl;
(iv) an aryl moiety with up to 6 ring carbon atoms, wherein the aryl ring of said moiety is optionally substituted with up to 3 substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N(R$^{2k}$)$_2$, wherein "R$^{2k}$" is, independently for each occurrence, —H or lower alkyl; (5) —N(R$^{3k}$)$_2$, wherein "R$^{3k}$" is, independently for each occurrence, —H or lower alkyl;
(v) a heteroaryl moiety with up to 4 carbon atoms and at least one heteroatom, wherein said heteroaryl moiety is optionally substituted with one or more substituents which are independently for each occurrence: (1) —CN; (2) —OH; (3) halogen; (4) cyclic-, branched-, or linear-alkyl of up to 4 carbon atoms, which alkyl moiety is optionally substituted with: —OH; —CN; halogen; or N(R$^{4k}$)$_2$, wherein "R$^{4k}$" is, independently for each occurrence, —H or lower alkyl; (5) —N(R$^{5k}$)$_2$, wherein "R$^{5k}$" is, independently for each occurrence, —H or lower alkyl; or
(vi) a heterocycloalkyl moiety with one or more heteroatoms which are N, O, or S;
(c) an aryl moiety, wherein the aryl ring of said moiety is optionally substituted with up to 3 substituents which are independently for each occurrence: (i) —CN; (ii) —OH; (iii) halogen; (iv) cyclic-, branched-, or linear-alkyl of up to 4 carbon atoms, which alkyl moiety is optionally substituted with: (1) —OH; (2) —CN; (3) halogen; or (4) —N(R$^{6k}$)$_2$, wherein "R$^{6k}$" is, independently for each occurrence, —H or lower alkyl; (v) —N(R$^{7k}$)$_2$, wherein "R$^{7k}$" is, independently for each occurrence, —H or lower alkyl; (vi) cyclic-, branched-, or linear-alkoxy of up to 4 carbon atoms;
(d) a heteroaryl moiety, wherein said heteroaryl moiety has up to 5 ring carbon atoms and at least one heteroatom which is N, S, or O, and wherein said heteroaryl moiety is optionally substituted on one or more ring carbon atoms with a substituent which is independently for each occurrence: (i) —CN; (ii) —OH; (iii) halogen; (iv) cyclic-, branched-, or linear-alkyl of up to 4 carbon atoms, which alkyl moiety is optionally substituted with one or more substituents which are independently: (1) —OH; (2) —CN; (3) halogen; or (4) —N(R$^{8k}$)$_2$, wherein "R$^{8k}$" is, independently for each occurrence, —H or lower alkyl; or (v) cyclic-, branched-, or linear-alkoxy of up to 4 carbon atoms; or
(e) a heterocycloalkyl moiety with up to 5 carbon atoms and one or more heteroatoms which are N, O, or S.

6. The compound of claim 1, or a pharmaceutically acceptable salt thereof, wherein R$^3$ is a moiety of Formula S1a:

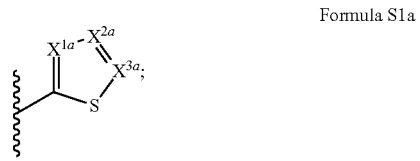

Formula S1a wherein: one of $X^{1a}$ to $X^{3a}$ is —N═ and the others are —CR$^8$═, where —R$^8$ is independently for each occurrence: (i) —H; (ii) lower-alkyl; or (iii) a halogen, and when a halogen R$^8$ is —Cl or —F.

7. The compound of claim 1, or a pharmaceutically acceptable salt thereof, wherein R$^3$ is a moiety of Formula S1b:

Formula S1b

8. A compound, or a pharmaceutically acceptable salt thereof, which is:

4-((((2S,4S)-2-benzyl-4-hydroxypyrrolidin-2-yl) methyl) amino)-5-chloro-2-fluoro-N-(thiazol-2-yl) benzenesulfonamide;

5-chloro-4-((((2S,4S)-2-(cyclobutylmethyl)-4-hydroxypyrrolidin-2-yl) methyl) amino)-2-fluoro-N-(thiazol-2-yl) benzenesulfonamide;

5-chloro-2-fluoro-4-((((2S,4S)-4-hydroxy-2-phenethylpyrrolidin-2-yl) methyl) amino)-N-(thiazol-2-yl) benzenesulfonamide;

4-((((2S,4S)-2-(4-bromobenzyl)-4-hydroxypyrrolidin-2-yl) methyl) amino)-5-chloro-2-fluoro-N-(thiazol-2-yl) benzenesulfonamide;

4-((((2S,4S)-2-(4-(aminomethyl) benzyl)-4-hydroxypyrrolidin-2-yl) methyl) amino)-5-chloro-2-fluoro-N-(thiazol-2-yl) benzenesulfonamide;

5-chloro-2-fluoro-4-((((2S,4S)-4-hydroxy-2-(3-phenylpropyl) pyrrolidin-2-yl) methyl) amino)-N-(thiazol-2-yl) benzenesulfonamide;

4-((((2S,4S)-2-(3-(aminomethyl) benzyl)-4-hydroxypyrrolidin-2-yl) methyl) amino)-5-chloro-2-fluoro-N-(thiazol-2-yl) benzenesulfonamide;

4-((((2S,4S)-2-(3-bromobenzyl)-4-hydroxypyrrolidin-2-yl) methyl) amino)-5-chloro-2-fluoro-N-(thiazol-2-yl) benzenesulfonamide;

5-chloro-2-fluoro-4-((((2S,4S)-4-hydroxy-2-(3-methoxybenzyl) pyrrolidin-2-yl) methyl) amino)-N-(thiazol-2-yl) benzenesulfonamide;

5-chloro-2-fluoro-4-((((2S,4S)-4-hydroxy-2-(3-methylbenzyl) pyrrolidin-2-yl) methyl) amino)-N-(thiazol-2-yl) benzenesulfonamide;

5-chloro-2-fluoro-4-((((2S,4S)-2-(3-fluorobenzyl)-4-hydroxypyrrolidin-2-yl) methyl) amino)-N-(thiazol-2-yl) benzenesulfonamide;

5-chloro-4-((((2S,4S)-2-(3-cyanobenzyl)-4-hydroxypyrrolidin-2-yl) methyl) amino)-2-fluoro-N-(thiazol-2-yl) benzenesulfonamide;

5-chloro-4-((((2S,4S)-2-(3,3-dimethylbutyl)-4-hydroxypyrrolidin-2-yl) methyl) amino)-2-fluoro-N-(thiazol-2-yl) benzenesulfonamide;

5-chloro-2-fluoro-4-((((2S,4S)-4-hydroxy-2-(4-(pyridin-2-yl) benzyl) pyrrolidin-2-yl) methyl) amino)-N-(thiazol-2-yl) benzenesulfonamide;

5-chloro-2-fluoro-4-((((2S,4S)-4-hydroxy-2-(4-(oxazol-2-yl) benzyl) pyrrolidin-2-yl) methyl) amino)-N-(thiazol-2-yl) benzenesulfonamide;

4-((((2S,4S)-2-(4-(1H-pyrazol-5-yl) benzyl)-4-hydroxypyrrolidin-2-yl) methyl) amino)-5-chloro-2-fluoro-N-(thiazol-2-yl) benzenesulfonamide; or 5-chloro-4-((((2S,4S)-2-(4-cyanobenzyl)-4-hydroxypyrrolidin-2-yl) methyl) amino)-2-fluoro-N-(thiazol-2-yl) benzenesulfonamide.

9. A pharmaceutical composition comprising at least one compound of claim 1, or a pharmaceutically acceptable salt thereof, and at least one pharmaceutically acceptable excipient.

10. The pharmaceutical composition of claim 9 comprising additionally an effective amount of at least one other pharmaceutically active ingredient which is: (i) an opiate agonist or antagonist; (ii) a calcium channel antagonist; (iii) an NMDA receptor agonist or antagonist; (iv) a COX-2 selective inhibitor; or (v) an NSAID (non-steroidal anti-inflammatory drug), and a pharmaceutically acceptable carrier.

11. A method of treating an inflammatory or neuropathic pain disorder, cough, or acute itch or chronic itch disorder comprising administering to a patient in need thereof a therapeutically effective amount of the compound of claim 10.

12. A formulation comprising an amount of the compound of claim 8, or a pharmaceutically acceptable salt thereof, which is sufficient to provide a therapeutic response in a subject in need of therapy for an inflammatory or neuropathic pain disorder, cough, or acute itch or chronic itch disorder.

13. A method of treating a neuropathic pain disorder comprising administering to a patient in need thereof a therapeutically effective amount of a formulation of claim 12.

14. The compound, or pharmaceutically acceptable salt thereof according to claim 1 for treating neuropathic pain disorders.

15. The compound, or pharmaceutically acceptable salt thereof according to claim 8 for treating neuropathic pain disorders.

* * * * *